US012590313B2

(12) United States Patent
Kumar et al.

(10) Patent No.: US 12,590,313 B2
(45) Date of Patent: ***Mar. 31, 2026

(54) METHODOLOGIES AND COMPOSITIONS FOR CREATING TARGETED RECOMBINATION AND BREAKING LINKAGE BETWEEN TRAITS

(71) Applicant: CORTEVA AGRISCIENCE LLC, Indianapolis, IN (US)

(72) Inventors: Sandeep Kumar, Johnston, IA (US); Ryan M. Lee, Brownsburg, IN (US); Stephen Novak, Westfield, IN (US); Andrew F. Worden, Indianapolis, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 692 days.

This patent is subject to a terminal disclaimer.

(21) Appl. No.: 18/051,194

(22) Filed: Oct. 31, 2022

(65) Prior Publication Data

US 2023/0117437 A1 Apr. 20, 2023

Related U.S. Application Data

(63) Continuation of application No. 16/994,734, filed on Aug. 17, 2020, now Pat. No. 11,519,000, which is a continuation of application No. 15/612,024, filed on Jun. 2, 2017, now Pat. No. 10,781,455.

(60) Provisional application No. 62/352,254, filed on Jun. 20, 2016.

(51) Int. Cl.
*C12N 15/82* (2006.01)

(52) U.S. Cl.
CPC ................................ *C12N 15/8213* (2013.01)

(58) Field of Classification Search
None
See application file for complete search history.

(56) References Cited

U.S. PATENT DOCUMENTS

| | | | |
|---|---|---|---|
| 7,273,578 B1 | 9/2007 | Slutsker et al. | |
| 7,273,758 B2 | 9/2007 | Nicolas et al. | |
| 10,781,455 B2 * | 9/2020 | Kumar | C12N 15/8213 |
| 11,519,000 B2 * | 12/2022 | Kumar | C12N 15/8213 |
| 2004/0023388 A1 | 2/2004 | Rozwadowski et al. | |
| 2011/0203012 A1 | 8/2011 | Dotson et al. | |
| 2011/0277189 A1 | 11/2011 | Kondo et al. | |
| 2014/0283166 A1 | 9/2014 | Chomet et al. | |
| 2015/0150160 A1 | 5/2015 | Sanchez-Fernandez et al. | |
| 2015/0351340 A1 | 12/2015 | Bundock et al. | |
| 2016/0257967 A1 | 9/2016 | Russell et al. | |

FOREIGN PATENT DOCUMENTS

| | | |
|---|---|---|
| EP | 3150626 A1 | 4/2017 |
| WO | 2004016795 A1 | 2/2004 |
| WO | 2013102875 A1 | 7/2013 |
| WO | 2014104878 A1 | 7/2014 |

OTHER PUBLICATIONS

Extended European Search Report for European Application No. 17815911.7, mailed Oct. 25, 2019, 07 Pages.
International Preliminary Report on Patentability for International Application No. PCT/US2017/035605, mailed Jan. 3, 2019, 08 Pages.
International Search Report and Written Opinion for International Application No. PCT/US2017/035605, mailed Aug. 25, 2017, 10 Pages.
Janisiw M.P., "Targeted Meiotic Recombination in *Arabidopsis thaliana*," Diplomarbeit, May 4, 2009, pp. 1-125, XP055244044, [Retrieved on Jan. 22, 2016] Retrieved from URL: http://othes. univie.ac.at/5477/1/2009-06-22_9804391.pdf.
Puchta H., et al., "Double-Strand Break-Induced Recombination between Ectopic Homologous Sequences in Somatic Plant Cells," Genetics, Jul. 1999, vol. 152, pp. 1173-1181.
Puchta H., et al., "From CentiMorgans to Base Pairs: Homologous Recombination in Plants," Trends in Plant Sciences, 1996, vol. 1, No. 10, pp. 340-348.
Siebert R., et al., "Efficient Repair of Genomic Double-Strand Breaks by Homologous Recombination between Directly Repeated Sequences in the Plant Genome," The Plant Cell, May 2002, vol. 14, pp. 1121-1131.
Wijnker E., et al., "Managing Meiotic Recombination in Plant Breeding," Trends in Plant Science, 2008, vol. 13, No. 12, pp. 640-646.

* cited by examiner

*Primary Examiner* — Matthew R Keogh

(57) ABSTRACT

The current disclosure relates to methods and compositions for improving plant varieties through plant breeding and plant genetics. For instance, the disclosure concerns increasing the recombination frequency of a heterozygous trait genetically linked to a second trait within plants. Further, the disclosure concerns breaking the genetic linkage between a first allele and a second allele.

24 Claims, 5 Drawing Sheets

Specification includes a Sequence Listing.

METHODOLOGIES AND COMPOSITIONS FOR CREATING TARGETED RECOMBINATION AND BREAKING LINKAGE BETWEEN TRAITS

This application claims a priority from U.S. Patent Application Ser. No. 16/994,73 U.S. Patent Publication No. 2020-0377899 A1) filed on Aug. 17, 2020, which is a Continuation of U.S. patent application Ser. No. 15/612,024 (U.S. Pat. No. 10,781,455) filed on Jun. 2, 2017, which is based on provisional application 62/352,254 which was filed in the U.S. Patent and Trademark Office on Jun. 20, 2016, the entire disclosure of which is hereby incorporated by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 28.2 KB.XML file named "78126-US-CNT2.xml" created on Nov. 16, 2022.

BACKGROUND

Modern plant breeding relies upon traditional breeding methodologies to develop and produce new varieties of plant species. Typically, the goal of plant breeding is to identify and selectively breed traits (as a single gene or multiple genes) from the parental lines into progeny plants. Such processes can be limited by the genetic linkage of desirable traits (e.g., traits which encode a phenotype with an agronomic advantage) with undesirable traits (e.g., traits which encode a phenotype that is deleterious or exemplifies an agronomic disadvantage).

Traditional plant breeding methodologies and compositions rely upon the analysis of large breeding populations to identify progeny plants that have broken linkage between a first trait located at a specific genomic locus and a second trait located at a specific genomic locus. Especially, where the first and second traits are tightly linked in the parent plant(s). Typically, the traits, which are located at distinct, specific genomic loci, can segregate and recombine into progeny via cross-over events which rely upon breakage and rejoining of the chromosome(s). The recombination frequency between the two traits can be calculated and determined as it is known that most cross-over events randomly occur along the length of the chromosome, and that the recombination frequency is a function of the distance between the first genomic locus that comprises a trait and second genomic locus that comprises a second trait. Accordingly, the closer two loci comprising two traits are in physical location with one another, the less likely it is that a cross-over between the two loci comprising the two traits will occur. The result is that the closely linked loci comprising tightly linked traits cannot be separated from one another are transmitted together to the progeny. Further compounding this process is the observation that some regions of the chromosome are characterized as genomic locations that inherently possess low levels of recombination. Genetically linked genomic loci comprising traits that are located in such genomic locations will remain genetically linked despite being located distally from one another, thereby being transmitted together to the progeny.

Methodologies and compositions that allow for increasing the recombination frequency between two traits located at distinct, separate genomic loci would allow for improved efficiencies in breaking the genetic linkage between the two traits. Resultantly, development of new plant varieties could be produced more expeditiously and at less cost, in the terms of both financial and resource costs. Ultimately, the tight linkage of desirable traits with undesirable traits can be broken so that plant breeders can produce new plant varieties or progeny that only containing the desirable traits that are desired for introgression into the progeny by the plant breeder, and any linkage drag associated with undesirable traits is eliminated.

Therefore, a need exists for new compositions and methodologies that allow for increasing the recombination frequency of a heterozygous trait linked to a locus within plants, and breaking the genetic linkage between a first heterozygous locus comprising a trait and a second locus comprising a trait.

BRIEF SUMMARY

In embodiments of the subject disclosure, the disclosure relates to a method for increasing the frequency of genetic recombination between a first locus genetically linked to a second locus within a genome of a plant, comprising: a) introducing a site specific nuclease into the genome of the plant; b) producing a double stranded break with the site specific nuclease in one of two homologous chromosomes; c) undergoing recombination within the plant genome; and, d) modifying the plant genome, wherein the modified plant genome comprises increased frequency of genetic recombination between the first locus and the second locus.

In an embodiment of this method, each of the loci encode at least one trait. In further embodiments, the recombination comprises meiotic recombination or mitotic recombination. In other embodiments, the frequency of genetic recombination is increased from 1.25 to 17.8 fold. In additional embodiments, the distance from the first locus to the second locus is from about 0.01 cM to about 500 cM. In further embodiments, the distance from the first locus to the second locus is from about 10 bp to about 10 Mbp. As an embodiment, the first locus is located on a first chromosome, and the second locus is located on a second chromosome. In an additional embodiment, the first locus to the second locus are present in a genomic location with low levels of recombination frequency. For example in an embodiment, the trait comprises a desirable trait or an undesirable trait. In such an example, the desirable trait or the undesirable trait is either a native trait or a transgenic trait. For instance the undesirable trait can be a reduced yield, reduced resistance to disease, reduced resistance to pests, reduced tolerance to herbicide tolerance, reduced growth, reduced size, reduced production of biomass, reduced amount of produced seeds, reduced resistance against salinity, reduced resistance against heat stress, reduced resistance against cold stress, reduced resistance against drought stress, and any combination thereof. Alternatively, the desirable trait can be a trait for increased yield, increased resistance to disease, increased resistance to pests, increased tolerance to herbicides, increased growth, increased size, increased production of biomass, increased amount of produced seeds, increased resistance against salinity, increased resistance against heat stress, increased resistance against cold stress, increased resistance against drought stress, and any combination thereof.

In further embodiments, the first locus comprises a polymorphic marker and the second locus comprise a trait. In an additional embodiment, the first locus comprises a polymorphic marker and the second locus comprises a polymorphic marker. In further embodiments, the plant may be a polyploid plant or a diploid plant.

In subsequent embodiments, the double stranded break is produced by a site specific nuclease. For example, the site specific nuclease can be a zinc finger nuclease, a TALEN nuclease, a CRISPR-Cas9 nuclease, a meganuclease, and a leucine zipper nuclease. In another embodiment, the site specific nuclease is delivered to a cell by intra-genomic recombination or via direct delivery.

In other embodiments, the method comprises: producing a progeny plant comprising the modified plant genome; crossing the progeny plant with another plant or to itself; and, generating a seed from the progeny plant. In an embodiment, the first loci comprising a first trait is heterozygous and located on the first homologous chromosome and independently segregates from the second loci comprising a second trait, thereby resulting in a progeny plant comprising only the first loci comprising the first trait located on the first homologous chromosome. In another embodiment, the second loci comprising a second trait is heterozygous and located on the second homologous chromosome and remains genetically linked to a third genomic locus, thereby resulting in a progeny plant comprising the second loci comprising the second trait genetically linked to a third genomic locus.

In subsequent embodiments, the plant is selected from a dicotyledonous plant or a monocotyledonous plant. For example the plant may be a tobacco plant, a soybean plant, a cotton plant, a *Brassica* plant, a corn plant, a sorghum plant, a wheat plant, or a rice plant.

The foregoing and other features will become more apparent from the following detailed description of several embodiments, which proceeds with reference to the accompanying figures.

4

Figure 5:
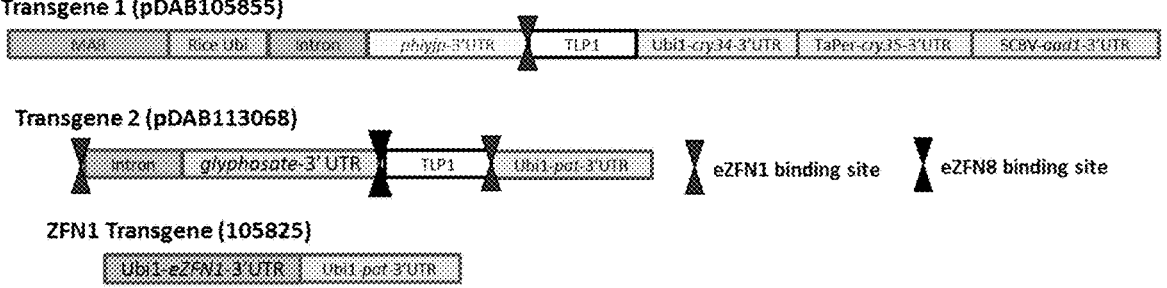

FIG. 5: This figure shows a schematic of the constructs used for the disclosure and the location of the eZFN1 binding site.

DETAILED DESCRIPTION

I. Overview

In the course of crop improvement projects involving selective breeding protocols, it is often desirable to disrupt the genetic linkage of a first genomic locus and a nearby second genomic locus. Especially when the second locus encodes a less desirable or even detrimental trait. For instance linkage drag may be described as the presence of genetic linkage between two traits, for example one desirable trait and the other an undesirable trait. As a consequence of this genetic linkage the two loci comprising the two traits are inherited together. Reliance upon natural recombination to generate the desirable recombinants is unsuitable if the two traits are tightly linked. Unfortunately, with the methods available in the art, removing the genetic linkage between such desired and undesired traits in a plant, and obtaining a plant with only the desired traits, has turned out to be difficult, time consuming, and in various cases impossible. If recombination frequency can be increased during the breeding procedure, in accordance with the methods of the present disclosure, recombination between the two loci comprising the traits would be at a higher frequency in the progeny, and plant breeder may develop a new progeny plants containing only the desirable trait in a less expensive and more efficient manner.

II. Definitions

Throughout the application, a number of terms are used. In order to provide a clear and consistent understanding of the specification and claims, including the scope to be given such terms, the following definitions are provided.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each of the two homologous chromosomes. A diploid plant species may have different alleles at corresponding loci on homologous chromosomes.

The term "backcross" refers to a cross between an offspring and one of its parents or an individual genetically identical to one of its parents. The term "backcross" encompasses "advanced backcross", meaning crosses between a backcross progeny and an inbred progenitor from a prior generation or an individual genetically identical to an inbred progenitors from a prior generation. The terms "backcross" or "advance backcross" are understood to include mating or assisted fertilization to generate backcross progeny. Preferred methods for assisted fertilization or reproduction include but are not limited to cloning, in vitro fertilization, or inter-cytoplasmic sperm injection. Methods for assisted fertilization are well known in the art (Thornton et al., 1999; Loutradis et al., 2000; Nakagata, 2000) U.S. Pat. Nos. 5,453,366, 5,541,081, 5,849,713). Backcrossing can be used to introduce one or more single locus conversions from one genetic background into another.

The term "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

The term "chromatid" refers to one of the two parts of a chromosome which exist after replication, there being one DNA double helix before replication, and two identical DNA double helices after replication, the basic elements of the two chromatids, attached at the centromere of a repli-cated chromosome; intrachromosomal recombination often causes a genetic endpoint.

The term "chromosome" is one of the self-replicating, thread- or rod-shaped structures within the nuclei of eukary-otic cells that consists of extremely condensed chromatin and contains genetic information for specific functions of the cell.

The term "crossing" refers to the mating of two parent plants.

The term "crossing over" or "crossover" refers to the reciprocal exchange of chromosome arms and can, for example, be visualized at late stages of meiotic prophase I as chiasmata.

The term "desirable trait" refers to any inheritable trait that confers an advantage or increased value to a commer-cially cultivated crop, while the phrase "undesirable trait" refers to any inheritable trait which is deleterious when expressed in the commercially cultivated crop. It is conceiv-able that in some cases, candidate genetic traits can be categorized as being both a "desirable trait" and an "unde-sirable trait" depending upon the application of the trait and the intent of the plant breeder. Specific examples of such commercially desirable and mitigating traits are provided herein.

The term "diploid" refers to a typical castor plant having two sets (2N) of chromosomes, whereby each set comprises 20 chromosomes. The diploid plant, as used herein is isogenic to the multiplied polyploid plant i.e., both sets of chromosomes contain essentially identical alleles in all locations. The diploid plant may be naturally occurring, genetically modified or a breeding product.

The term "dominant trait" refers to diploid or other polyploid organisms a trait that is phenotypically manifest in either the heterozygous of homozygous state, and refers to alleles that fully manifest their phenotypic expressions over another recessive allele.

The term "expression of a gene" refers to the process wherein a DNA region, which is operably linked to appro-priate regulatory regions, particularly a promoter, is tran-scribed into an RNA, which is biologically active, i.e. which is capable of being translated into a biologically active protein or peptide (or active peptide fragment) or which is active itself (e.g. in posttranscriptional gene silencing or RNAi). The coding sequence is preferably in sense-orien-tation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation.

The term "fold change" is a measure describing how much a quantity changes going from an initial to a final value. For example, an initial value of 30 and a final value of 60 corresponds to a fold change of 1 (or equivalently, a change to 2 times), or in common terms, a two-fold increase.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites.

The term "genome", as used herein, relates to a material or mixture of materials, containing genetic material from an organism. The term "genomic DNA" as used herein refers to deoxyribonucleic acids that are obtained from an organism. The terms "genome" and "genomic DNA" encompass hereditary information of an individual typically encoded in nucleic acids, either DNA, or RNA, and including both genes and non-coding sequences. The genome may refer to the nucleic acids making up one set of chromosomes of an organism (haploid genome) or both sets of chromosomes of an organism (diploid genome) depending on the context in which it is used.

The term "genetic recombination" used herein has a broad meaning indicating a phenomenon of DNA cleavage/rejoin-ing involving DNAs. The meaning of the term "genetic recombination" used in the present disclosure encompasses homologous recombination, non-homologous recombina-tion, gene conversion, inversion, unequal crossover, cross-over, translocation, copy number change, chromosome fusion, and mutation. In addition, the term "rearrangement" refers to a situation in which the increased frequency of "genetic recombination" causes a recombination between existing genomic sequences, resulting in partial or complete alteration of the genomic sequence.

The term "genetically linked" refers to a first locus being spaced within a given genetic distance from a second locus so that the two loci are inherited together in a progeny plant, such traits are in linkage disequilibrium and statistically determined not to assort independently.

The term "heterozygote" or "heterozygous" means a diploid or polyploid individual cell or plant having different alleles (forms of a given gene) at least at one locus, for instance the term denotes a genetic condition in which different alleles reside at the same loci on homologous chromosomes.

The term "homologous" in the context of a pair of homologous chromosomes refers to a pair of chromosomes from an individual that are similar in length, gene position and centromere location, and that line up and synapse during meiosis. In an individual, one chromosome of a pair of homologous chromosomes comes from the mother of the individual (i.e., is "maternally-derived"), whereas the other chromosomes of the pair comes from the father (i.e., is "paternally-derived"). In the context of genes, the term "homologous" refers to a pair of genes where each gene resides within each homologous chromosome at the same position and has the same function.

The term "homologous recombination" refers to a recip-rocal exchange at corresponding positions between between homologous chromosomes, such as between non-sister chro-matids of homologous chromosomes during meiosis. Homologous recombination can also occur in somatic cells during mitosis (somatic crossing over).

The term "homozygote" or "homozygous" means an individual cell or plant having the same alleles at one or more loci, for instance the term denotes a genetic condition in which identical alleles reside at the same loci on homologous chromosomes.

The term "intra-genomic delivery" refers to the delivery of a gene expression cassette, wherein the gene expression cassette is incorporated within the plant genome, from one plant to a second plant (either a progeny or another parent) by crossing of the two plants.

The term "introgression" refers to the transmission of a desired allele of a genetic locus from one genetic background to another. For example, introgression of a desired allele at a specified locus can occur via a sexual cross between two plants, where at least one of the plants has the desired allele within its genome. The allele is introgressed into the progeny. In another example, transmission of an allele can occur by recombination between two donor genomes in vitro, e.g., in a fused protoplast, where at least one of the donor protoplasts has the desired allele in its genome. The desired allele can be, e.g., a transgene or a selected allele of a marker or quantitative trait locus.

The term an "isolated nucleic acid sequence" refers to a nucleic acid sequence which is no longer in the natural environment from which it was isolated, e.g. the nucleic acid sequence in a bacterial host cell or in the plant nuclear or plastid genome.

The term "linkage disequilibrium" refers to a non-random association of alleles from two or more loci. It implies that a group of marker alleles or alleles have been inherited together.

The term "linkage drag" refers to the (usually undesirable) effects of traits linked to the desirable traits being introgressed into a progeny plant. As a result of the linkage drag, the undesirable trait is inherited with the desirable trait as a result of being genetically linked to the undesirable trait.

The term "locus" refers to the position of a gene or any genetic site that has been defined genetically, for instance on a chromosome or gene map. A locus may be a gene, or part of a gene, or a DNA sequence that has some regulatory role, and may be occupied by different sequences. The relative distance between two loci can be given by referring to the Morgan unit, but a locus can also be identified by the nature of the neighboring genes. In the methods of the subject disclosure, the first and the second locus are different, i.e. if the first loci is at a specific position on a first chromosome, the second loci is at a specific position on the first chromosome which locus has a specific distance from the first loci such that recombination frequency between the loci can be determined.

The term "meiosis" or "meiotic" refers to a two-stage process of nuclear division that reduces the somatic chromosome number (2n) to half (n) and which is usually followed by gamete formation. In the first stage of meiosis the chromosome number is reduced, wherein in the second stage of meiosis there is an equational division of the chromosome resulting in four daughter nuclei, each carrying one chromatid.

Although the term "mitosis" or "mitotic" is commonly used synonomously with the term "cell division", mitosis correctly refers to only one phase of the cell division process: the process in which the sister chromatids are partitioned equally between the two daughter cells. In eukaryotic cells, mitosis is followed by cytokinesis, which is the process by which the cell cytoplasm is cleaved into two distinct but genetically identical daughter cells.

The term "modify", "modified", "modifying" or "modification" is not especially limited as used herein, includes an act defined by one or more of changing, controlling, altering, attenuating, transforming, or making different. In one embodiment, the term "modify", "modified", "modifying" or "modification" includes chemical modification and biological modification. In another embodiment, the term "modify", "modified", "modifying" or "modification" includes altering a plant genome so that the genome does not contain the same original genetic material as the result of deletion, substitution, additions, or other rearrangement.

The term "morgan" or "map unit" each refer to a unit for expressing the relative distance between genes on a chromosome. One Morgan unit (cM) indicates a recombination frequency of 100%. A centimorgan (cM) indicates a recombination frequency of 1%.

The term "nucleic acid sequence" (or nucleic acid molecule) refers to a DNA or RNA molecule in single or double stranded form, particularly a DNA molecule encoding a protein or protein fragment according to the disclosure.

The term "native trait" refers to a naturally occurring recognized non-transgenic plant phenotype which is heritable and can be used in several varieties of at least one plant species. Alternatively a native trait is man-made and can be generated through mutagenesis of plants. A native trait is often introgressed in a variety or plant species of choice by breeding. Introgression of a native trait can be carried out with the aid of molecular markers flanking the locus or loci comprising the native trait of interest.

The term "phenotype" means the observable characters of an individual cell, cell culture, plant, or group of plants which results from the interaction between that individual's genetic makeup (i.e., genotype) and the environment.

The term "plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing. "Plant cell(s)" include protoplasts, gametes, suspension cultures, microspores, pollen grains, etc., either in isolation or within a tissue, organ or organism.

The term "polyploid" refers to a plant with three or more sets of chromosomes (e.g., 3N, 4N, 5N, 6N and more). According to some embodiments of this aspect of the present disclosure, the polyploid plant is an autopolyploid.

The term "progeny" refers to the direct offspring of a particular plant (selfcross) or pair of plants (cross-pollinated) and includes all of the plants and seeds of all subsequent generations resulting from a particular designated generation. The descendants can be, for example, of the $F_1$, the $F_2$ or any subsequent generation.

The term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells, while a "tissue preferred" promoter is preferentially, but not exclusively, active in certain tissues or cells. A "promoter which is active in plants or plant cells" is a promoter which has the capability of initiating transcription in plant cells.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

The term "recessive trait" refers to diploid or other polyploid organisms a trait that is phenotypically manifest in the homozygous state but is masked in the presence of its dominant allele.

The term "recombinant" as used herein means that something has been recombined, so that when made in reference to a nucleic acid construct the term refers to a molecule that is comprised of nucleic acid sequences that are joined together or produced by means of molecular biological techniques. The term "recombinant" or "recombination" when made in reference to genetic composition refers to a gamete or progeny with new combinations of alleles that did not occur in the parental genomes.

The term "recombination" refers to a process by which the linkage of genes is altered. Due to the recombination process, the combination of genes in a progeny molecule, cell or organism has a different pattern than the combination of genes in the parent molecules, cells or organisms. The recombination may occur due to the exchange of DNA sequences between two chromosomes or the new association of genes in a recombinant. Within the meaning of the present disclosure, the recombination is due to the exchange of DNA sequences between two chromosomes by the process of crossing-over, i.e. the reciprocal exchange of segments of homologous chromosomes by symmetrical breakage and crosswise recombination. Hence, the terms "recombination" and "crossing-over" may be used interchangeably.

The term "recombination frequency" or "crossing-over frequency" or "frequency of genetic recombination" is used to denote the frequency by which crossing-over and recombination occurs between two loci on a chromosome. The recombination frequency is usually calculated as the percentage of individuals having the recombined phenotype per total number of individuals analyzed. In the process of the disclosure it is calculated as the number of individuals showing expression of the reporter protein per total number of individuals analyzed in a test cross population such as the pollen of the F1 progeny or the plants of the F2 progeny, as discussed further below. The "basal" recombination frequency is the recombination frequency in plants which are grown under standard conditions, which have not been mutagenized or treated with biotic or abiotic stimuli and which have not been transformed with expression cassettes other than the first and second and optionally third and fourth expression cassette. The "induced" recombination frequency is the recombination frequency in plants which contain a double strand break within one of the homologus chromosomes, thereby influencing recombination between the genetically linked loci.

The term "separating" means one or more process used to partially or completely isolate from one another one or more components, and/or one or more process that results in one or more components being no longer located in the same place. The one or more components optionally include, but are not limited to, one or more chromosome types, or single chromosomes, or single copies of a chromosome type.

Processes include, but are not limited to, manual, automatic, semi-automatic, remote-controlled, and/or robotic. Illustrative embodiments of such processes include but are not limited to fluorescence activated cell sorting (FACS).

The term "transgenic plant" or "transformed plant" refers herein to a plant or plant cell having been transformed with a chimeric gene. Said chimeric gene may or may not be integrated into the plant's genome. In a preferred embodiment it is not integrated. A transgenic plant cell may refer to a plant cell in isolation or in tissue culture, or to a plant cell contained in a plant or in a differentiated organ or tissue, and both possibilities are specifically included herein. Hence, a reference to a plant cell in the description or claims is not meant to refer only to isolated cells or protoplasts in culture, but refers to any plant cell, wherever it may be located or in whatever type of plant tissue or organ it may be present.

The term "variety" means a subdivision of a species, consisting of a group of individuals within the species which are distinct in form or function from other similar arrays of individuals.

III. Embodiments

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein.

Provided are methods and compositions for increasing the frequency of genetic recombination between genetically linked loci within a plant genome, wherein the loci encodes a trait, comprises an allele, or comprises a polymorphic marker. Further provided are methods and compositions for increasing the amount of segregation between genetically linked loci within a plant genome, wherein the loci encodes a trait, comprises an allele, or comprises a polymorphic marker. Also provided are methods and compositions for increasing the genetic linkage disequilibrium between genetically linked loci within a plant genome, wherein the loci encodes a trait, comprises an allele, or comprises a polymorphic marker. Generally provided are methods and compositions for reducing genetic linkage between genetically linked alleles within a plant genome, wherein the allele encodes a trait, comprises a loci, or comprises a polymorphic marker In an aspect, the subject disclosure relates to increasing genetic recombination between two genomic loci. The distance between chromosomal loci is governed by recombination frequency between homologous chromosomes on which the loci are located. By monitoring the frequency of genetic recombination between two loci, a plant breeder can determine how many successive generations of backcrossing are required to break the linkage of a first locus with a second locus, so that only the first locus is passed onto progeny plants. In an embodiment, the genetic linkage between two genetically linked loci is disrupted by introducing a double strand break in one of two homologous chromosomes, thereby resulting in increased genetic recombination. The increase in genetic recombination may be determined as follows.

In an aspect, increasing the frequency of genetic recombination is any percentage that is greater than the frequency of genetic recombination naturally occurring between two linked loci within a plant genome. The frequency of genetic recombination naturally occurring between two linked loci within a plant genome can be determined as a percentage of genetic recombination. In some aspects, methods of the subject disclosure result to increase this frequency of genetic recombination from a 1.25 fold to a 17.8 fold increase in genetic recombination. In some embodiments of this aspect, methods to increase this frequency of genetic recombination result in a 1.25 fold increase in genetic recombination. In other embodiments of this aspect, methods to increase this frequency of genetic recombination result in a 2 fold increase in genetic recombination. In further embodiments of this aspect, methods to increase this frequency of genetic recombination result in a 2.25 fold increase in genetic recombination. In embodiments of this aspect, methods to increase this frequency of genetic recombination result in a 3.2 fold increase in genetic recombination. In embodiments of this aspect, methods to increase this frequency of genetic recombination result in a 8 fold increase in genetic recombination. In additional embodiments of this aspect, methods to increase this frequency of genetic recombination result in a 8.6 fold increase in genetic recombination. In embodiments of this aspect, methods to increase this frequency of genetic recombination result in a 13 fold increase in genetic recombination. In embodiments of this aspect, methods to increase this frequency of genetic recombination result in a 17.8 fold increase in genetic recombination. In further embodiments of this aspect, methods to increase this frequency of genetic recombination result in greater than a 17.75 fold increase in genetic recombination. Further increases in the frequency of genetic recombination that result from methods of the subject disclosure increase genetic recombination of greater than a 1.25 fold, 1.5 fold, 1.75 fold, 2 fold, 2.25 fold, 2.5 fold, 2.75 fold, 3 fold, 3.25 fold, 3.5 fold, 3.75 fold, 4 fold, 4.25 fold, 4.5 fold, 4.75 fold, 5 fold, 5.25 fold, 5.5 fold, 5.75 fold, 6 fold, 6.25 fold, 6.75 fold, 7 fold, 7.25 fold, 7.5 fold, 7.75 fold, 8 fold, 8.25 fold, 8.75 fold, 9 fold, 9.25 fold, 9.5 fold, 9.75 fold, 10 fold, 11 fold, 12 fold, 13 fold 14 fold, 15 fold, 16 fold, 17 fold, 18 fold, 19 fold, 20 fold, 21 fold, 22 fold, 23 fold, 24 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, or 100 fold increase.

In an aspect, increasing the frequency of genetic recombination is any percentage that is greater than the frequency of genetic recombination that naturally occurs between two linked loci within a plant genome. The frequency of genetic recombination that naturally occurring between two linked loci within a plant genome can be determined as a percentage of genetic recombination. The frequency of genetic recombination frequency can be calculated by dividing the number of recombinant offspring containing only the first loci or only the second loci, alone and unlinked by the total number of offspring observed. For this disclosure the percentage of genetic recombination that naturally occurred between two linked loci within the plant genome was calculated at 3.5% as an exemplary frequency of genetic recombination. In some aspects, methods of the subject disclosure result to increase this frequency of genetic recombination from 4.4% to a 62.3% genetic recombination. In some embodiments of this aspect, methods to increase this frequency of genetic recombination result in 4.4% genetic recombination. In other embodiments of this aspect, methods to increase this frequency of genetic recombination result in 7.1% genetic recombination. In further embodiments of this aspect, methods to increase this frequency of genetic recombination result in 7.2% genetic recombination. In embodiments of this aspect, methods to increase this frequency of genetic recombination result in 7.9% genetic recombination. In embodiments of this aspect, methods to increase this frequency of genetic recombination result in 11.5% genetic recombination. In additional embodiments of this aspect, methods to increase this frequency of genetic recombination result in 27.8% genetic recombination. In embodiments of this aspect, methods to increase this frequency of genetic recombination result in 30.2% genetic recombination. In embodiments of this aspect, methods to increase this frequency of genetic recombination result in 45.6% genetic recombination. In embodiments of this aspect, methods to increase this frequency of genetic recombination result in 62.3% genetic recombination. In some embodiments of this aspect, methods to increase this frequency of genetic recombination result in greater than a 4.4% increase in genetic recombination. In other embodiments of this aspect, methods to increase this frequency of genetic recombination result in greater than a 7.1% increase in genetic recombination. In further embodiments of this aspect, methods to increase this frequency of genetic recombination result in greater than a 7.2% increase in genetic recombination. In embodiments of this aspect, methods to increase this frequency of genetic recombination result in a greater than 7.9% increase in genetic recombination. In embodiments of this aspect, methods to increase this frequency of genetic recombination result in greater than a 11.5% increase in genetic recombination. In additional embodiments of this aspect, methods to increase this frequency of genetic recombination result in greater than a 27.8% increase in genetic recombination. In embodiments of this aspect, methods to increase this frequency of genetic recombination result in greater than a 30.2% increase in genetic recombination. In embodiments of this aspect, methods to increase this frequency of genetic recombination result in greater than a 45.6% genetic recombination. In embodiments of this aspect, methods to increase this frequency of genetic recombination result in greater than a 62.0% increase in genetic recombination. Further increases in the frequency of genetic recombination that result from methods of the subject disclosure increase genetic recombination of greater than 4.4%, 4.5%, 4.75%, 5%, 5.25%, 5.5%, 5.75%, 6%, 6.25%, 6.75%, 7%, 7.25%, 7.5%, 7.75%, 8%, 8.25%, 8.75%, 9%, 9.25%, 9.5%, 9.75%, 10%, 11%, 12%, 13%, 14%, 15%, 16%, 17%, 18%, 19, 20%, 21%, 22%, 23%, 24%, 25%, 30%, 35%, 40%, 45%, 50%, 55%, 60%, 65%, 70%, 75%, 80%, 85%, 90%, 95%, or 99%.

In another aspect, the subject disclosure relates to reducing the genetic linkage between two linked loci. In an embodiment, the genetic linkage between two genetically linked loci is disrupted by introducing a double strand break in one of two homologous chromosomes, thereby resulting in increased genetic recombination and a subsequent decrease in genetic linkage between two linked loci.

In another aspect, the subject disclosure relates to increasing the segregation between two linked loci. In an embodiment, the ability of two genetically linked loci to segregate as only a single locus that is transmitted progeny plants is increased by introducing a double strand break in one of two homologous chromosomes, thereby resulting in increased genetic recombination and a subsequent increase in segregation.

In another aspect, the subject disclosure relates to increasing the genetic linkage disequilibrium between two linked loci. In an embodiment, the ability of two genetically linked loci to remain genetically linked as only a single locus that is transmitted progeny plants is increased by introducing a double strand break in one of two homologous chromosomes, thereby resulting in increased genetic recombination and a subsequent increase in genetic linkage disequilibrium.

In another aspect, the subject disclosure relates to recombination occurring cell division phase. In an embodiment recombination may occur during meiosis. In a further embodiment recombination may occur during mitosis. Meiosis and meiotic recombination are intricate processes which have been studied to different degrees and at different levels in different organisms. During meiosis and mitosis recombination occurs between homologous chromosomes by crossing-over mechanisms, resulting in the exchange of DNA segments between the homologous chromosomes.

Mitosis and meiosis are in many ways opposite processes. A principal role of DNA recombination in mitotic cells is to preserve the fidelity of genetic information and ensure that it is faithfully reproduced and passed on to daughter cells. In contrast, DNA recombination during meiosis acts to create new permutations of genetic information by facilitating reshuffling or intermixing of the maternal and paternal genomes during gamete formation to enable production of offspring with novel genomes as compared to either parent. The different purposes of DNA recombination in meiotic versus mitotic cells are reflected in the very different rolls and mechanisms of homologous recombination in each cell type.

There is a fundamental mechanistic distinction between the primary processes of homologous recombination in meiotic (germ-line) cells compared to mitotic (vegetative/somatic) cells. In meiotic cells, homologous recombination occurs primarily between non-sister chromatids (to shuffle the genome), whereas in mitotic cells homologous recombination occurs primarily between sister chromatids (to correct genomic errors). Sister chromatids are replicated copies of a particular maternal or paternal chromosome. Recombination between non-sister chromatids (i.e. between a paternal chromatid and a maternal chromatid) occurs 500-1000 fold more frequently in meiotic cells versus mitotic cells. The meiotic process of non-sister chromatid exchange (NSCE) facilitates novel recombination of the genetic information from two parents of the organism. In contrast, the mitotic process of sister-chromatid exchange (SCE) resulting from recombination-mediated repair is a primary mechanism for maintaining genome fidelity throughout a multi-cellular organism.

In specific embodiments, the recombination occurs during a cytological phase of meiosis. During meiosis a number of cytological phases are distinguished and for each phase a number of mutants has been described in plants. During the initial phase called meiotic Prophase a number of stages are discerned. During the initial stage called Leptotene, the individual chromosomes which have been replicated and which consist of two sister chromatids start to condense and become shorter and thicker. Simultaneously, the nuclear envelope starts to disintegrate and the homologous chromosomes start to associate. The next stage is called Zygotene in which the chromosomes are fully condensed and in which the homologous chromosomes align and start to form the so-called synaptonemal complex (SC). The dif1/syn1 mutant of *Arabidopsis* is impaired in the formation of the SC (Bhatt, A. M. et al (1999) Plant J. 19, 463-472; Bal, X. et al (1999) Plant Cell 11, 417-430). The DIF1/SYN1 gene products are homologous to the yeast cohesin REC8/RAD21 which function in synapsis and recombination. At Pachytene the formation of the SC is completed for all chromosomes. At this stage meiotic recombination occurs which is initiated by the formation of double-stranded breaks followed by chromatid exchange between homologous chromosomes. The physical links that are established between the non-sister chromatids and which persist even in the absence of the synaptonemal complex are called chiasmata. During Diplotene and Diakinesis the chromosomes fully condense, the nuclear envelope has disappeared and the spindle fibers have been formed. Subsequently during Metaphase I, the pairs of homologous chromosomes are located in the equatorial plane of the cell. Then, during Anaphase I, the homologous chromosomes, each consisting of two sister chromatids which may have undergone a number of recombination events and are held together by a centromere, move towards the opposite cellular poles. During Telophase I, the polar movement is completed, the spindle disappears and the cell starts to divide.

Subsequently, these cells enter Prophase II that is characterized by the alignment of the condensed chromosomes on the equatorial plane. A spindle complex is being formed. During Metaphase II the chromosomes are fully aligned at the equatorial plane and the spindle complex is completed. During the next phase, called Anaphase II, the centromeres divide and the sister chromatids move towards opposite poles. In Telophase II this movement process is completed, the spindle complex starts disappearing and cell division initiates. Subsequently, the chromosomes resume their Interphase appearance characterized by uncoiled chromosomes located inside the nuclear envelope.

The end product of meiosis II is a set of four genetically distinct haploid cells, which can undergo mitosis to develop into gametophytes. The gametophytes produce the gametes, which upon fusion leads to the formation of a zygote, which develops, into an embryo that can grow out into the next generation sporophyte.

The genetic variation, which occurs in the sporophyte, is determined by the genotypes of the female and male gametes that fused upon the formation of the zygote. Therefore this genetic variation is created during the formation of the female and male spores during meiosis which leads to genetic re-assortment of the original parental chromosomes as well as chromosomal regions due to recombination events.

In an aspect, the disclosure relates to genetically linked loci. Generally, a locus is any polynucleotide sequence that is physically located on a chromosome. As an embodiment, the locus can span any range of polynucleotide base pairs from 1 base pair to 1,0000,000 base pairs (i.e., 1 Mbp) in length. In a further embodiment, the locus may comprise an allele. In another embodiment, the locus may comprise a trait. In an additional embodiment, the locus may comprise a polymorphic marker.

In further embodiments, a trait can include a transgenic trait. Transgenic traits that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene encodes a selectable marker or a gene product conferring insecticidal resistance, herbicide tolerance, small RNA expression, nitrogen use efficiency, water use efficiency, or nutritional quality.

1. Insect Resistance

Various insect resistance coding sequences are an embodiment of a transgenic trait. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1 Ab(truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A(a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance coding sequences are an embodiment of a transgenic trait. Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF_W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), 1s+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait coding sequences are an embodiment of a transgenic trait. Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding protein coding sequences are an embodiment of a transgenic trait. Exemplary DNA binding protein coding sequences are known in the art. As embodiments of DNA binding protein coding sequences that can be operably linked to the regulatory elements of the subject disclosure, the following types of DNA binding proteins can include; Zinc Fingers, Talens, CRISPRS, and meganucleases. The above list of DNA binding protein coding sequences is not meant to be limiting. Any DNA binding protein coding sequences is encompassed by the present disclosure. 5. Small RNA Various small RNAs are an embodiment of a transgenic trait. Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes are an embodiment of a transgenic trait. Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvylshikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, or transgene is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166,302, and 5,380,831, herein incorporated by reference.

In further embodiments, a trait can include a non-transgenic trait, such as a native trait or an endogenous trait. Exemplary native traits can include yield traits, resistance to disease traits, resistance to pests traits, tolerance to herbicide tolerance traits, growth traits, size traits, production of biomass traits, amount of produced seeds traits, resistance against salinity traits, resistance against heat stress traits, resistance against cold stress traits, resistance against drought stress traits, male sterility traits, waxy starch traits, modified fatty acid metabolism traits, modified phytic acid metabolism traits, modified carbohydrate metabolism traits, modified protein metabolism traits, and any combination of such traits.

In further embodiments, exemplary native traits can include early vigor, stress tolerance, drought tolerance, increased nutrient use efficiency, increased root mass and increased water use efficiency. Additional exemplary native traits can include resistance to fungal, bacterial and viral pathogens, plant insect resistance; modified flower size, modified flower number, modified flower pigmentation and shape, modified leaf number, modified leaf pigmentation and shape, modified seed number, modified pattern or distribution of leaves and flowers, modified stem length between nodes, modified root mass and root development characteristics, and increased drought, salt and antibiotic tolerance. Fruit-specific native traits include modified lycopene content, modified content of metabolites derived from lycopene including carotenes, anthocyanins and xanthophylls, modified vitamin A content, modified vitamin C content, modified vitamin E content, modified fruit pigmentation and shape, modified fruit ripening characteristics, fruit resistance to fungal, bacterial and viral pathogens, fruit resistance to insects, modified fruit size, and modified fruit texture, e.g., soluble solids, total solids, and cell wall components.

In an aspect, the native traits may be specific to a particular crop. Exemplary native traits in corn can include the traits described in U.S. Pat. No. 9,288,955, herein incorporated by reference in its entirety. Exemplary native traits in soybean can include the traits described in U.S. Pat. No. 9,313,978, herein incorporated by reference in its entirety. Exemplary native traits in cotton can include the traits described in U.S. Pat. No. 8,614,375, herein incorporated by reference in its entirety. Exemplary native traits in sorghum can include the traits described in U.S. Pat. No. 9,080,182, herein incorporated by reference in its entirety. Exemplary native traits in wheat can include the traits described in U.S. Patent Application No. 2015/0040262, herein incorporated by reference in its entirety. Exemplary native traits in wheat can include the traits described in U.S. Pat. No. 8,927,833, herein incorporated by reference in its entirety. Exemplary native traits in *Brassica* plants can include the traits described in U.S. Pat. No. 8,563,810, herein incorporated by reference in its entirety. Exemplary native traits in tobacco plants can include the traits described in U.S. Pat. No. 9,096,864, herein incorporated by reference in its entirety.

In a further aspect, exemplary polymorphic markers can include genetic marker profiles obtained by techniques such as restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) also referred to as microsatellites, or single nucleotide polymorphisms (SNPs). For example, see Cregan et al. (1999) "An Integrated Genetic Linkage Map of the Soybean Genome" Crop Science 39:1464-1490, and Berry et al. (2003) "Assessing Probability of Ancestry Using Simple Sequence Repeat Profiles: Applications to Maize Inbred Lines and Soybean Varieties" Genetics 165:331-342, each of which are incorporated by reference herein in their entirety.

Genetic maps defined with polymorphic markers may also be used with the disclosed method. This process of marker assisted selection or marker assisted breeding involves linking polymorphic markers to a desired trait or allele by determining the frequency of co-inheritance of polymorphic markers with the trait/allele. Once a polymorphic markers has been found which is inherited at high frequency with the target trait, it can be used as a molecular probe to screen a DNA library of the organism to identify a fragment of DNA which encodes the cognate gene or quantitative trait loci. One major difficulty with marker assisted selection or marker assisted breeding is that the relationship between genetic distance and physical distance can vary between species and even between different regions of the genome in a given species. Therefore a molecular marker may show absolute linkage to the target trait locus but it may be physically hundreds of kilobases away from the actual gene of interest. This makes identifying and introgressing the actual gene responsible for the trait difficult because there may be vast stretches of DNA to evaluate in order to identify the trait/allele. In addition, one might map more than one polymorphic marker showing absolute linkage to the target trait locus. However, using a reasonable population size, it may not be possible to identify which marker is physically closer to the target gene. Thus, while one marker may be 10 kilobases from the target gene and the other is 400 kilobases from the target gene, with conventional methods relying on natural levels of recombination frequency there may be no way of differentiating which of the two markers should be used to most efficiently clone the target gene. It would therefore be beneficial to map-based cloning projects to utilize the present method of the subject disclosure to provide elevated recombination levels so as to increase precision in determining genetic distance between polymorphic markers and target trait loci.

Means of performing genetic polymorphic marker profiles using polymorphisms are well known in the art. SSRs, RFLPs, RAPDs, AP-PCT, DAF, SCARs, AFLPs, and SNPs are genetic markers based on polymorphisms in repeated nucleotide sequences, such as microsatellites. The polymorphisms may refers to single nucleotide exchanges, or di-, tri- or tetra-nucleotide repeats within a genome. The repeat region may vary in length between genotypes while the DNA flanking the repeat is conserved such that the primers will work in a plurality of genotypes. A polymorphism between two genotypes represents repeats of different lengths between the two flanking conserved DNA sequences. A marker system based on SSRs, RFLPs, RAPDs, AP-PCT, DAF, SCARs, AFLPs, or SNPs can be highly informative in linkage analysis relative to other marker systems in that multiple alleles may be present. Another advantage of this type of marker is that, through use of flanking primers, detection of polymorphic markers can be achieved, for example, by the polymerase chain reaction (PCR). The PCR detection is done by the use of two oligonucleotide primers flanking the polymorphic segment of the polymorphism followed by DNA amplification. This step involves repeated cycles of heat denaturation of the DNA followed by annealing of the primers to their complementary sequences at low temperatures, and extension of the annealed primers with DNA polymerase. Size separation of DNA fragments on agarose or polyacrylamide gels following amplification, comprises the major part of the methodology. Such selection and screening methodologies are well known to those skilled in the art. Molecular confirmation methods that can be used to identify transgenic plants are known to those with skill in the art. Several exemplary methods are further described below.

Molecular Beacons have been described for use in sequence detection, such as a polymorphic sequence, a trait, or an allele. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence, such as a polymorphic sequence, a trait, or an allele. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence, such as a polymorphic sequence, a trait, or an allele. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTOO13®, BOBO®, YOYO®, and TOTO®.

In further embodiments, Next Generation Sequencing (NGS) can be used for detection of a sequence, such as a polymorphic sequence, a trait, or an allele. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLiD™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generate sequencing reads. DNA fragments of 300-800 bp or libraries containing fragments of 3-20 kb can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems™ is a short read technology. This NGS technology uses fragmented double stranded DNA that are up to 10 kb in length. The system uses sequencing by ligation of dye-labelled oligonucleotide primers and emulsion PCR to generate one billion short reads that result in a total sequence output of up to 30 gigabases per run.

tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotides that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

In further embodiments, exemplary alleles are included in the subject disclosure. A polymorphism is thus said to be allelic, in that, due to the existence of the polymorphism, some members of a species may have the "standard" sequence (i.e. the standard "allele") whereas other members may have a variant sequence (i.e., a variant "allele"). Thus, as used herein, an allele is one of two or more alternative versions of a gene or other genetic region at a particular location on a chromosome. In the simplest case, only one variant sequence may exist, and the polymorphism is thus said to be bi-allelic. In other cases, the species' population may contain multiple alleles, and the polymorphism is termed tri-allelic, etc.

A single gene encoding trait or genetic region may have multiple different unrelated polymorphisms. For example, it may have a one bi-allelic polymorphism at one site, another bi-allelic polymorphism at another site and a multi-allelic polymorphism at another site. When all the sequences for a group of alleles at a chromosomal locus in a plant are the same, the alleles are said to be homozygous at that locus.

When the sequence of any allele at a particular locus in a plant is different, the population of alleles is said to be heterozygous at that locus. In an embodiment, the locus may be present in the plant genome as a heterozygous locus. In a further embodiment, the locus may be comprised of a trait that is present in the plant genome as a heterozygous trait. In a further embodiment, the locus may be comprised of an allele that is present in the plant genome as a heterozygous allele. In a further embodiment, the locus may be comprised of a polymorphic marker that is present in the plant genome as a heterozygous polymorphic marker.

In another aspect, the subject disclosure relates to desirable traits. In an embodiment, the desirable trait may be closely linked to another undesirable trait. The plant breeder decides which trait is desirable and which trait is undesirable. Generally, it is the goal of the plant breeder to produce a progeny plant that possess the desirable trait(s) and does not possess the undesirable trait(s). The methods of the disclosure provide a solution to overcome the tight genetic linkage between two such traits (i.e., a desirable trait genetically linked to an undesirable trait). The genetic linkage of a desirable trait to an undesirable trait results in the inheritance of the two traits into progeny plants, and is commonly referred to as linkage drag. In an embodiment, the desirable trait may be a native trait. In a further embodiment, the desirable trait may be a transgenic trait. In an embodiment, the undesirable trait may be a native trait. In another embodiment, the undesirable trait may be a transgenic trait.

Exemplary undesirable traits can include reduced yield traits, reduced resistance to disease traits, reduced resistance to pests traits, reduced tolerance to herbicide tolerance traits, reduced growth traits, reduced size traits, reduced production of biomass traits, reduced amount of produced seeds traits, reduced resistance against salinity traits, reduced resistance against heat stress traits, reduced resistance against cold stress traits, reduced resistance against drought stress traits, male sterility traits, waxy starch traits, modified fatty acid metabolism traits, modified phytic acid metabolism traits, modified carbohydrate metabolism traits, modified protein metabolism traits, and any combination of such traits.

Exemplary desirable traits can include increased yield traits, increased resistance to disease traits, increased resistance to pests traits, increased tolerance to herbicide tolerance traits, increased growth traits, increased size traits, increased production of biomass traits, increased amount of produced seeds traits, increased resistance against salinity traits, increased resistance against heat stress traits, increased resistance against cold stress traits, increased resistance against drought stress traits, male sterility traits, waxy starch traits, modified fatty acid metabolism traits, modified phytic acid metabolism traits, modified carbohydrate metabolism traits, modified protein metabolism traits, and any combination of such traits.

In another aspect, the subject disclosure relates to a method to select recessive traits and to segregate these traits away from dominant traits in progeny plants. In an embodiment, the recessive trait may be present in a plant genome as a heterozygous trait with a dominant trait. The plant breeder may decide to produce progeny plants that possess the recessive trait. The methods of the disclosure provide a solution to pass the recessive trait into progeny plants. For example, a double strand break may be specifically introduced into the dominant trait so that only the recessive trait is passed to the progeny plants. In an embodiment, a first allele may encode a dominant trait and a second allele may encode a recessive trait. In further embodiments, a method to introduce a double strand break in the dominant trait results in the production of progeny plants that contain the recessive trait.

In a further aspect, the subject disclosure relates to a method to select dominant traits and to segregate these traits away from recessive traits in progeny plants. In an embodiment, the dominant trait may be present in a plant genome as a heterozygous trait with a recessive trait. The plant breeder may decide to produce progeny plants that possess the dominant trait. The methods of the disclosure provide a solution to pass the dominant trait into progeny plants. For example, a double strand break may be specifically introduced into the recessive trait so that only the dominant trait is passed to the progeny plants. In an embodiment, a first allele may encode a recessive trait and a second allele may encode a dominant trait. In further embodiments, a method to introduce a double strand break in the recessive trait results in the production of progeny plants that contain the dominant trait.

In further aspects, the locus (including alleles, traits, and/or polymorphic markers) may be located at a specific position on the chromosome. In some embodiments, the distance between a first locus (including alleles, traits, and/or polymorphic markers) and second locus (including alleles, traits, and/or polymorphic markers) on the chromosome may be spaced so that the first locus is physically separated from the second locus. In an embodiment, the distance between a first locus (including alleles, traits, and/or polymorphic markers) and second locus (including alleles, traits, and/or polymorphic markers) may range from 0.01 cM to 500 cM. In further embodiments, the distance between a first locus (including alleles, traits, and/or polymorphic markers) and second locus (including alleles, traits, and/or polymorphic markers) may be at least 0.01 cM. In embodiments, the distance between a first locus (including alleles, traits, and/or polymorphic markers) and second locus (including alleles, traits, and/or polymorphic markers) may be at least 0.05 cM. In embodiments, the distance between a first locus (including alleles, traits, and/or polymorphic markers) and second locus (including alleles, traits, and/or polymorphic markers) may be at least 0.1 cM. In embodiments, the distance between a first locus (including alleles, traits, and/or polymorphic markers) and second locus (including alleles, traits, and/or polymorphic markers) may be at least 0.2 cM. In embodiments, the distance between a first locus (including alleles, traits, and/or polymorphic markers) and second locus (including alleles, traits, and/or polymorphic markers) may be at least 0.3 cM. In embodiments, the distance between a first locus (including alleles, traits, and/or polymorphic markers) and second locus (including alleles, traits, and/or polymorphic markers) may be at least 0.4 cM. In embodiments, the distance between a first locus (including alleles, traits, and/or polymorphic markers) and second locus (including alleles, traits, and/or polymorphic markers) may be at least 0.5 cM. In embodiments, the distance between a first locus (including alleles, traits, and/or polymorphic markers) and second locus (including alleles, traits, and/or polymorphic markers) may be at least 0.6 cM. In embodiments, the distance between a first locus (including alleles, traits, and/or polymorphic markers) and second locus (including alleles, traits, and/or polymorphic markers) may be at least 0.7 cM. In embodiments, the distance between a first locus (including alleles, traits, and/or polymorphic markers) and second locus (including alleles, traits, and/or polymorphic markers) may be at least 0.8 cM. In embodiments, the distance between a first locus (including alleles, traits, and/or polymorphic markers) and second locus (including alleles, traits, and/or polymorphic markers) may be at least 0.9 cM. In embodiments, the distance between a first locus (including alleles, traits, and/or polymorphic markers) and second locus (including alleles, traits, and/or polymorphic markers) may be at least 1.0 cM. In embodiments, the distance between a first locus (including alleles, traits, and/or polymorphic markers) and second locus (including alleles, traits, and/or polymorphic markers) may be at least 2.0 cM. In embodiments, the distance between a first locus (including alleles, traits, and/or polymorphic markers) and second locus (including alleles, traits, and/or polymorphic markers) may be at least 3.0 cM. In embodiments, the distance between a first locus (including alleles, traits, and/or polymorphic markers) and second locus (including alleles, traits, and/or polymorphic markers) may be at least 4.0 cM. In embodiments, the distance between a first locus (including alleles, traits, and/or polymorphic markers) and second locus (including alleles, traits, and/or polymorphic markers) may be at least 5.0 cM. In embodiments, the distance between a first locus (including alleles, traits, and/or polymorphic markers) and second locus (including alleles, traits, and/or polymorphic markers) may be at least 6.0 cM. In embodiments, the distance between a first locus (including alleles, traits, and/or polymorphic markers) and second locus (including alleles, traits, and/or polymorphic markers) may be at least 7.0 cM. In embodiments, the distance between a first locus (including alleles, traits, and/or polymorphic markers) and second locus (including alleles, traits, and/or polymorphic markers) may be at least 8.0 cM. In embodiments, the distance between a first locus (including alleles, traits, and/or polymorphic markers) and second locus (including alleles, traits, and/or polymorphic markers) may be at least 9.0 cM. In embodiments, the distance between a first locus (including alleles, traits, and/or polymorphic markers) and second locus (including alleles, traits, and/or polymorphic markers) may be at least 10.0 cM. In embodiments, the distance between a first locus (including alleles, traits, and/or polymorphic markers) and second locus (including alleles, traits, and/or polymorphic markers) may be at least 11.0 cM. In embodiments, the distance between a first locus (including alleles, traits, and/or polymorphic markers) and second locus (including alleles, traits, and/or polymorphic markers) may be at least 12.0 cM. In embodiments, the distance between a first locus (including alleles, traits, and/or polymorphic markers) and second locus (including alleles, traits, and/or polymorphic markers) may be at least 13.0 cM. In embodiments, the distance between a first locus (including alleles, traits, and/or polymorphic markers) and second locus (including alleles, traits, and/or polymorphic markers) may be at least 14.0 cM. In embodiments, the distance between a first locus (including alleles, traits, and/or polymorphic markers) and second locus (including alleles, traits, and/or polymorphic markers) may be at least 15.0 cM. In embodiments, the distance between a first locus (including alleles, traits, and/or polymorphic markers) and second locus (including alleles, traits, and/or polymorphic markers) may be at least 16.0 cM. In embodiments, the distance between a first locus (including alleles, traits, and/or polymorphic markers) and second locus (including alleles, traits, and/or polymorphic markers) may be at least 17.0 cM. In embodiments, the distance between a first locus (including alleles, traits, and/or polymorphic markers) and second locus (including alleles, traits, and/or polymorphic markers) may be at least 18.0 cM. In embodiments, the distance between a first locus (including alleles, traits, and/or polymorphic markers) and second locus (including alleles, traits, and/or polymorphic markers) may be at least 19.0 cM. In embodiments, the distance between a first locus (including alleles, traits, and/or polymorphic markers) and second locus (including alleles, traits, and/or polymorphic markers) may be at least 20.0 cM. In embodiments, the distance between a first locus (including alleles, traits, and/or polymorphic markers) and second locus (including alleles, traits, and/or polymorphic markers) may be at least 25.0 cM. In embodiments, the distance between a first locus (including alleles, traits, and/or polymorphic markers) and second locus (including alleles, traits, and/or polymorphic markers) may be at least 30.0 cM. In embodiments, the distance between a first locus (including alleles, traits, and/or polymorphic markers) and second locus (including alleles, traits, and/or polymorphic markers) may be at least 35.0 cM. In embodiments, the distance between a first locus (including alleles, traits, and/or polymorphic markers) and second locus (including alleles, traits, and/or polymorphic markers) may be at least 40.0 cM. In embodiments, the distance between a first locus (including alleles, traits, and/or polymorphic markers) and second locus (including alleles, traits, and/or polymorphic markers) may be at least 45.0 cM. In embodiments, the distance between a first locus (including alleles, traits, and/or polymorphic markers) and second locus (including alleles, traits, and/or polymorphic markers) may be at least 50.0 cM. In embodiments, the distance between a first locus (including alleles, traits, and/or polymorphic markers) and second locus (including alleles, traits, and/or polymorphic markers) may be at least 55.0 cM. In embodiments, the distance between a first locus (including alleles, traits, and/or polymorphic markers) and second locus (including alleles, traits, and/or polymorphic markers) may be at least 60.0 cM. In embodiments, the distance between a first locus (including alleles, traits, and/or polymorphic markers) and second locus (including alleles, traits, and/or polymorphic markers) may be at least 65.0 cM. In embodiments, the distance between a first locus (including alleles, traits, and/or polymorphic markers) and second locus (including alleles, traits, and/or polymorphic markers) may be at least 70.0 cM. In embodiments, the distance between a first locus (including alleles, traits, and/or polymorphic markers) and second locus (including alleles, traits, and/or polymorphic markers) may be at least 75.0 cM. In embodiments, the distance between a first locus (including alleles, traits, and/or polymorphic markers) and second locus (including alleles, traits, and/or polymorphic markers) may be at least 80.0 cM. In embodiments, the distance between a first locus (including alleles, traits, and/or polymorphic markers) and second locus (including alleles, traits, and/or polymorphic markers) may be at least 85.0 cM. In embodiments, the distance between a first locus (including alleles, traits, and/or polymorphic markers) and second locus (including alleles, traits, and/or polymorphic markers) may be at least 90.0 cM. In embodiments, the distance between a first locus (including alleles, traits, and/or polymorphic markers) and second locus (including alleles, traits, and/or polymorphic markers) may be at least 95.0 cM. In embodiments, the distance between a first locus (including alleles, traits, and/or polymorphic markers) and second locus (including alleles, traits, and/or polymorphic markers) may be at least 100.0 cM. In embodiments, the distance between a first locus (including alleles, traits, and/or polymorphic markers) and second locus (including alleles, traits, and/or polymorphic markers) may be at least 125.0 cM. In embodiments, the distance between a first locus (including alleles, traits, and/or polymorphic markers) and second locus (including alleles, traits, and/or polymorphic markers) may be at least 150.0 cM. In embodiments, the distance between a first locus (including alleles, traits, and/or polymorphic markers) and second locus (including alleles, traits, and/or polymorphic markers) may be at least 175.0 cM. In embodiments, the distance between a first locus (including alleles, traits, and/or polymorphic markers) and second locus (including alleles, traits, and/or polymorphic markers) may be at least 200.0 cM. In embodiments, the distance between a first locus (including alleles, traits, and/or polymorphic markers) and second locus (including alleles, traits, and/or polymorphic markers) may be at least 225.0 cM. In embodiments, the distance between a first locus (including alleles, traits, and/or polymorphic markers) and second locus (including alleles, traits, and/or polymorphic markers) may be at least 250.0 cM. In embodiments, the distance between a first locus (including alleles, traits, and/or polymorphic markers) and second locus (including alleles, traits, and/or polymorphic markers) may be at least 275.0 cM. In embodiments, the distance between a first locus (including alleles, traits, and/or polymorphic markers) and second locus (including alleles, traits, and/or polymorphic markers) may be at least 300.0 cM. In embodiments, the distance between a first locus (including alleles, traits, and/or polymorphic markers) and second locus (including alleles, traits, and/or polymorphic markers) may be at least 325.0 cM. In embodiments, the distance between a first locus (including alleles, traits, and/or polymorphic markers) and second locus (including alleles, traits, and/or polymorphic markers) may be at least 350.0 cM. In embodiments, the distance between a first locus (including alleles, traits, and/or polymorphic markers) and second locus (including alleles, traits, and/or polymorphic markers) may be at least 375.0 cM. In embodiments, the distance between a first locus (including alleles, traits, and/or polymorphic markers) and second locus (including alleles, traits, and/or polymorphic markers) may be at least 400.0 cM. In embodiments, the distance between a first locus (including alleles, traits, and/or polymorphic markers) and second locus (including alleles, traits, and/or polymorphic markers) may be at least 425.0 cM. In embodiments, the distance between a first locus (including alleles, traits, and/or polymorphic markers) and second locus (including alleles, traits, and/or polymorphic markers) may be at least 450.0 cM. In embodiments, the distance between a first locus (including alleles, traits, and/or polymorphic markers) and second locus (including alleles, traits, and/or polymorphic markers) may be at least 475.0 cM. In embodiments, the distance between a first locus (including alleles, traits, and/or polymorphic markers) and second locus (including alleles, traits, and/or polymorphic markers) may be at least 499.0 cM.

In an aspect, the distance between a first locus (including alleles, traits, and/or polymorphic markers) and second locus (including alleles, traits, and/or polymorphic markers) may range from 10 bp to 10 Mbp. In further embodiments, the distance between a first locus (including alleles, traits, and/or polymorphic markers) and second locus (including alleles, traits, and/or polymorphic markers) may be at least 10 bp. In further embodiments, the distance between a first locus (including alleles, traits, and/or polymorphic markers) and second locus (including alleles, traits, and/or polymorphic markers) may be at least 20 bp. In further embodiments, the distance between a first locus (including alleles, traits, and/or polymorphic markers) and second locus (including alleles, traits, and/or polymorphic markers) may be at least 30 bp. In further embodiments, the distance between a first locus (including alleles, traits, and/or polymorphic markers) and second locus (including alleles, traits, and/or polymorphic markers) may be at least 40 bp. In further embodiments, the distance between a first locus (including alleles, traits, and/or polymorphic markers) and second locus (including alleles, traits, and/or polymorphic markers) may be at least 50 bp. In further embodiments, the distance between a first locus (including alleles, traits, and/or polymorphic markers) and second locus (including alleles, traits, and/or polymorphic markers) may be at least 60 bp. In further embodiments, the distance between a first locus (including alleles, traits, and/or polymorphic markers) and second locus (including alleles, traits, and/or polymorphic markers) may be at least 70 bp. In further embodiments, the distance between a first locus (including alleles, traits, and/or polymorphic markers) and second locus (including alleles, traits, and/or polymorphic markers) may be at least 80 bp. In further embodiments, the distance between a first locus (including alleles, traits, and/or polymorphic markers) and second locus (including alleles, traits, and/or polymorphic markers) may be at least 90 bp. In further embodiments, the distance between a first locus (including alleles, traits, and/or polymorphic markers) and second locus (including alleles, traits, and/or polymorphic markers) may be at least 100 bp. In further embodiments, the distance between a first locus (including alleles, traits, and/or polymorphic markers) and second locus (including alleles, traits, and/or polymorphic markers) may be at least 200 bp. In further embodiments, the distance between a first locus (including alleles, traits, and/or polymorphic markers) and second locus (including alleles, traits, and/or polymorphic markers) may be at least 300 bp. In further embodiments, the distance between a first locus (including alleles, traits, and/or polymorphic markers) and second locus (including alleles, traits, and/or polymorphic markers) may be at least 400 bp. In further embodiments, the distance between a first locus (including alleles, traits, and/or polymorphic markers) and second locus (including alleles, traits, and/or polymorphic markers) may be at least 500 bp. In further embodiments, the distance between a first locus (including alleles, traits, and/or polymorphic markers) and second locus (including alleles, traits, and/or polymorphic markers) may be at least 600 bp. In further embodiments, the distance between a first locus (including alleles, traits, and/or polymorphic markers) and second locus (including alleles, traits, and/or polymorphic markers) may be at least 700 bp. In further embodiments, the distance between a first locus (including alleles, traits, and/or polymorphic markers) and second locus (including alleles, traits, and/or polymorphic markers) may be at least 800 bp. In further embodiments, the distance between a first locus (including alleles, traits, and/or polymorphic markers) and second locus (including alleles, traits, and/or polymorphic markers) may be at least 900 bp. In further embodiments, the distance between a first locus (including alleles, traits, and/or polymorphic markers) and second locus (including alleles, traits, and/or polymorphic markers) may be at least 1 Kbp. In further embodiments, the distance between a first locus (including alleles, traits, and/or polymorphic markers) and second locus (including alleles, traits, and/or polymorphic markers) may be at least 10 Kbp. In further embodiments, the distance between a first locus (including alleles, traits, and/or polymorphic markers) and second locus (including alleles, traits, and/or polymorphic markers) may be at least 100 Kbp. In further embodiments, the distance between a first locus (including alleles, traits, and/or polymorphic markers) and second locus (including alleles, traits, and/or polymorphic markers) may be at least 1,000 Kbp. In further embodiments, the distance between a first locus (including alleles, traits, and/or polymorphic markers) and second locus (including alleles, traits, and/or polymorphic markers) may be at least 1 Mbp.

In traditional genetics, the recombination frequency between two distinct genetic loci is used as a measure of genetic distance between these loci on a particular chromosome. The maximum frequency of recombination between any two loci is 50%, the same value that would be observed if the genes were on non-homologous chromosomes and assorted independently. A recombination frequency of 50% occurs when the genes are so far apart on the chromosome that at least one crossing-over almost always occurs between them. In an aspect, the recombination frequency between a first locus (including alleles, traits, and/or polymorphic markers) and second locus (including alleles, traits, and/or polymorphic markers) may range from 1% to 50%. In further embodiments, the recombination frequency may be at least 1%. In further embodiments, the recombination frequency may be at least 2%. In further embodiments, the recombination frequency may be at least 3%. In further embodiments, the recombination frequency may be at least 4%. In further embodiments, the recombination frequency may be at least 5%. In further embodiments, the recombination frequency may be at least 6%. In further embodiments, the recombination frequency may be at least 7%. In further embodiments, the recombination frequency may be at least 8%. In further embodiments, the recombination frequency may be at least 9%. In further embodiments, the recombination frequency may be at least 10%. In further embodiments, the recombination frequency may be at least 15%. In further embodiments, the recombination frequency may be at least 20%. In further embodiments, the recombination frequency may be at least 22.5%. In further embodiments, the recombination frequency may be at least 25%. In further embodiments, the recombination frequency may be at least 27.5%. In further embodiments, the recombination frequency may be at least 30%. In further embodiments, the recombination frequency may be at least 32.5%. In further embodiments, the recombination frequency may be at least 35%. In further embodiments, the recombination frequency may be at least 37.5%. In further embodiments, the recombination frequency may be at least 40%. In further embodiments, the recombination frequency may be at least 42.5%. In further embodiments, the recombination frequency may be at least 45%. In further embodiments, the recombination frequency may be at least 47.5%. In further embodiments, the recombination frequency may be at least 49%.

In further embodiments, the first locus (including alleles, traits, and/or polymorphic markers) may be located at a specific position on a first chromosome, and the second locus (including alleles, traits, and/or polymorphic markers) on the chromosome may be located at a specific position on a second chromosome that is non-homologous to the first chromosome.

In other embodiments, the first locus (including alleles, traits, and/or polymorphic markers) may be located at a specific position on a first homologous chromosome, and the second locus (including alleles, traits, and/or polymorphic markers) on the chromosome may be located at a specific position on a second homologous chromosome.

In an aspect, the disclosure relates to a plant genome. As an embodiment of the subject disclosure the genome is contained of homologous chromosomes. During recombination, either in meiosis or mitosis, different loci along the homologous chromosomes will recombine thereby resulting in genetic segregation between the loci. Typically, the loci on a homologous chromosome will segregate independently depending upon the physical spacing between the two loci.

The greater the distance between the two loci, the greater likelihood that the loci will segregate in progeny plants. Conversely, if the two loci are located closely to one another, it is less likely that the loci will segregate in progeny plants. Such loci, i.e., that are located closely to one another, are described in the art as being genetically linked. It may be desirable to the plant breeder to increase the frequency of genetic recombination between two genetically linked loci by introducing a double strand break in only one of the two homologous chromosomes. In an embodiment, the paternal homologous chromosome is cleaved with a site specific nuclease to introduce a double strand break in only the paternal homologous chromosome, and the maternal homologous chromosome is not cleaved with a site specific nuclease. In another embodiment, the maternal homologous chromosome is cleaved with a site specific nuclease to introduce a double strand break in only the maternal homologous chromosome, and the paternal homologous chromosome is not cleaved with a site specific nuclease.

In an aspect, the disclosure relates to a polyploid plant genome. Many plants possess complex genomes that contain more than two copies of homologous chromosomes. For example; maize, tomato, sorghum and rice are typically diploid; banana and watermelon are typically triploid; durum wheat, cotton and potato are typically tetraploid; bread wheat and kiwifruit are typically hexaploid; and, strawberry and sugarcane are typically octoploid. It may be desirable to the plant breeder to increase the frequency of genetic recombination between two genetically linked loci by introducing a double strand break in only one of the many homologous chromosomes present in a polyploid plant species. In an embodiment, a first chromosome is cleaved with a site specific nuclease to introduce a double strand break in only one of the many homologous chromosomes present in a polyploid plant species, and the other homologous chromosomes are not cleaved with the site specific nuclease. In an embodiment the recombination frequency between the loci located close to the double strand break of the cleaved homologous chromosome is increased so that the frequency of genetic recombination between two linked loci is increased as a result of the double strand break that is produced in only one of the many homologous chromosomes present in a polyploid plant species. In a further embodiment the genetic linkage between two linked loci is broken as a result of the double strand break that is produced in only one of the many homologous chromosomes present in a polyploid plant species. In another embodiment the linkage between two linked loci is disrupted as a result of the double strand break that is produced in only one of the many homologous chromosomes present in a polyploid plant species.

In another aspect, the subject disclosure relates to site specific nuclease for introduction of a double stranded DNA break. In accordance with one embodiment a site specific nuclease can include a zinc finger nuclease (ZFN) that is used to introduce a double strand break in a targeted genomic locus to facilitate the insertion of a nucleic acid of interest. Selection of a target site within the selected genomic locus for binding by a zinc finger domain can be accomplished, for example, according to the methods disclosed in U.S. Pat. No. 6,453,242, the disclosure of which is incorporated herein, that also discloses methods for designing zinc finger proteins (ZFPs) to bind to a selected sequence. It will be clear to those skilled in the art that simple visual inspection of a nucleotide sequence can also be used for selection of a target site. Accordingly, any means for target site selection can be used in the methods described herein.

For ZFP DNA-binding domains, target sites are generally composed of a plurality of adjacent target subsites. A target subsite refers to the sequence, usually either a nucleotide triplet or a nucleotide quadruplet which may overlap by one nucleotide with an adjacent quadruplet that is bound by an individual zinc finger. See, for example, WO 02/077227, the disclosure of which is incorporated herein. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also consistent with the subject disclosure.

In accordance with one embodiment, it is not necessary for a target site to be a multiple of three nucleotides. In cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. One nonlimiting example would be a four-finger binding domain that binds to a 13-nucleotide target site comprising, in sequence, two contiguous 3-nucleotide subsites, an intervening nucleotide, and two contiguous triplet subsites.

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an $\alpha$-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell. Preferably, the zinc finger protein is non-naturally occurring in that it is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534, 261; 6,599,692; 6,503,717; 6,689,558; 7,030,215; 6,794, 136; 7,067,317; 7,262,054; 7,070,934; 7,361,635; 7,253, 273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-Csml, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128.

As another alternative, the DNA-binding domain may be derived from a leucine zipper protein. Leucine zippers are a class of proteins that are involved in protein-protein interactions in many eukaryotic regulatory proteins that are important transcription factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix. The DNA binding specificity of leucine zippers can be utilized in the DNA-binding domains disclosed herein.

In some embodiments, the DNA-binding domain is an engineered domain from a TAL effector derived from the plant pathogen *Xanthomonas* (see, Miller et al. (2011) Nature Biotechnology 29(2):143-8; Boch et al, (2009) Science 29 Oct 2009 (10.1126/science.117881) and Moscou and Bogdanove, (2009) Science 29 Oct. 2009 (10.1126/science.1178817; and U.S. Patent Publication Nos. 20110239315, 20110145940 and 20110301073).

The CRISPR (Clustered Regularly Interspaced Short Palindromic Repeats) Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) Science 337, p. 816-821, Jinek et al, (2013), eLife 2:e00471, and David Segal, (2013) eLife 2:e00563). Thus, the CRISPR Cas system can be engineered to create a double-stranded break (DSB) at a desired target in a genome, and repair of the DSB can be influenced by the use of repair inhibitors to cause an increase in error prone repair. Other CRISPR Cas systems are known in the art and include CRISPR CasX, CRIXPR CasY, CRISP Cpf1, and other similarly functioning enzymes.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. The Cas protein is deployed in mammalian cells (and putatively within plant cells) by co-expressing the Cas nuclease with guide RNA. Two forms of guide RNAs can be used to facilitate Cas-mediated genome cleavage as disclosed in Le Cong, F., et al., (2013) *Science* 339(6121):819-823.

In other embodiments, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease (ZFN). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort et al. (1997) Nucleic Acids Res. 25:3379-3388. Additional enzymes which cleave DNA are known (e.g., 51 Nuclease; mung bean nuclease; pancreatic DNase I; micro-coccal nuclease; yeast HO endonuclease; see also Linn et al. (eds.) Nucleases, Cold Spring Harbor Laboratory Press, 1993). Non limiting examples of homing endonucleases and meganucleases include I-SceI, I-CeuI, PI-PspI, PI-Sce, I-SceIV, I-Csml, I-PanI, I-SceII, I-Ppol, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain. Exemplary Type IIS restriction enzymes are described in International Publication WO 2007/014275, incorporated by reference herein in its entirety.

To enhance cleavage specificity, cleavage domains may also be modified. In certain embodiments, variants of the cleavage half-domain are employed these variants minimize or prevent homodimerization of the cleavage half-domains. Non-limiting examples of such modified cleavage half-domains are described in detail in WO 2007/014275, incorporated by reference in its entirety herein. In certain embodiments, the cleavage domain comprises an engineered cleavage half-domain (also referred to as dimerization domain mutants) that minimize or prevent homodimerization. Such embodiments are known to those of skill the art and described for example in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Additional engineered cleavage half-domains of FokI that form obligate heterodimers can also be used in the ZFNs described herein. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499. In one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey'" mutations (see Guo et al, (2010) J. Mol. Biol. 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055. Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Distance between target sites refers to the number of nucleotides or nucleotide pairs intervening between two target sites as measured from the edges of the sequences nearest each other. In certain embodiments in which cleavage depends on the binding of two zinc finger domain/cleavage half-domain fusion molecules to separate target sites, the two target sites can be on opposite DNA strands. In other embodiments, both target sites are on the same DNA strand. For targeted integration into the optimal genomic locus, one or more ZFPs are engineered to bind a target site at or near the predetermined cleavage site, and a fusion protein comprising the engineered DNA-binding domain and a cleavage domain is expressed in the cell. Upon binding of the zinc finger portion of the fusion protein to the target site, the DNA is cleaved, preferably via a double-stranded break, near the target site by the cleavage domain.

In certain embodiments, two fusion proteins, each comprising a DNA-binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two DNA-binding domains. One or both of the DNA-binding domains can be engineered. See, also, U.S. Pat. No. 7,888,121; U.S. Patent Publication 20050064474 and International Patent Publications WO05/084190, WO05/014791 and WO 03/080809.

The site specific nucleases as described herein can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA. In an aspect, the subject disclosure relates to the direct delivery of the site specific nuclease is delivered to a plant cell. In another aspect, the subject disclosure relates to the intra-genomic delivery of the site specific nuclease is delivered to a plant cell.

Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more donor polynucleotide acid sequences in the genome of the transgenic plant.

The intra-genomic delivery or the direct delivery of nucleic acids may be introduced into a plant cell in embodiments of the disclosure by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301);, by acceleration of DNA-coated particles (See, e.g., U.S. Pat. Nos. 5,015,580, 5,550,318, 5,538,880, 6,160, 208, 6,399,861, and 6,403,865) and by Nanoparticles, nano-carriers and cell penetrating peptides (WO201126644A2; WO2009046384A1; WO2008148223A1) in the methods to deliver DNA, RNA, Peptides and/or proteins or combinations of nucleic acids and peptides into plant cells.

The most widely-utilized method for introducing an expression vector into plants is based on the natural transformation system of *Agrobacterium. A. tumefaciens* and *A. rhizogenes* are plant pathogenic soil bacteria that genetically transform plant cells. The $T_i$ and $R_i$ plasmids of *A. tumefaciens* and *A. rhizogenes*, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the disclosure.

Thus, in some embodiments, a plant transformation vector is derived from a Ti plasmid of *A. tumefaciens* (See, e.g., U.S. Pat. Nos. 4,536,475, 4,693,977, 4,886,937, and 5,501,967; and European Patent EP 0 122 791) or a $R_i$ plasmid of *A. rhizogenes*. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as *Sinorhizobium, Rhizobium*, and *Mesorhizobium* that naturally interact with plants can be modified to mediate gene transfer to a number of diverse plants. These plant-associated symbiotic bacteria can be made competent for gene transfer by acquisition of both a disarmed Ti plasmid and a suitable binary vector.

In addition, once a site specific nuclease has been stably integrated into the genome of a first plant, the nuclease can be bred into a progeny plant and deployed to bind and cleave a specific target sight by crossing the first and second parent plant. In such an example, the genome of the first parent plant does not contain a target sequence that is bound and cleaved by a site specific nuclease. However, the second parent plant does contain a target sequence that is bound and cleaved by the site specific nuclease located in the first parent plant. Accordingly, the breeding of the first and second parent plant allows for the site specific nuclease of the first parent plant to be functional in progeny plants that inherit both the site specific nuclease from the first parent plant and the target sequence of the second parent plant. In such an embodiment, the site specific nuclease is delivered to a plant cell by intra-genomic recombination.

In an aspect of the subject disclosure, the methods provided are applicable foe producing a progeny plant comprising a modified genome. The development of progeny plants is typically achieved through conventional plant breeding techniques. Such breeding techniques are well known to one skilled in the art. For a discussion of plant breeding techniques, see Poehlman (1995) Breeding Field Crops. AVI Publication Co., Westport Conn, 4$^{th}$ Edit, herein incorporated by reference in its entirety. Backcrossing methods may be used to introduce a gene into the plants. This technique has been used for decades to introduce traits into a plant. An example of a description of this and other plant breeding methodologies that are well known can be found in references such as Poelman, supra, and Plant Breeding Methodology, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonre-current parent.

Certain embodiments relate to processes of making crosses using a plant of an embodiment of this disclosure as at least one parent. For example, particular embodiments relate to an $F_1$ hybrid plant having as one or both parents any of the plants exemplified herein. Other embodiments relate to seed produced by such $F_1$ hybrids. Still other embodiments relate to a method for producing an $F_1$ hybrid seed by crossing an exemplified plant with a different (e.g. in-bred parent) plant and harvesting the resultant hybrid seed. Other embodiments relate to an exemplified plant that is either a female parent or a male parent. Characteristics of the resulting plants may be improved by careful consideration of the parent plants.

As an embodiment of the subject disclosure, a progeny plant can be bred by first sexually crossing a first parental plant and a second parental plant, thereby producing a plurality of first progeny plants; then selecting a first progeny plant that contains the loci of interest unlinked to the second loci; selfing the first progeny plant, thereby producing a plurality of second progeny plants; and then selecting from the second progeny plants a plant that contains the loci of interest unlinked to the second loci. These steps can further include the back-crossing of the first progeny plant or the second progeny plant to the second parental plant or a third parental plant. A crop comprising seeds of particular embodiments, or progeny thereof, can then be planted.

It is also to be understood that two plants can also be crossed to produce offspring that contain independently segregating genes as a result of the disclosed method. Selfing of appropriate progeny can produce plants that are homozygous for both added, exogenous genes. Back-crossing to a parental plant and out-crossing with another plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

Methodologies for regenerating plants are known to those of ordinary skill in the art and can be found, for example, in: Plant Cell and Tissue Culture, 1994, Vasil and Thorpe Eds. Kluwer Academic Publishers and in: Plant Cell Culture Protocols (Methods in Molecular Biology 111, 1999 Hall Eds Humana Press). The plant described herein can be cultured in a fermentation medium or grown in a suitable medium such as soil. In some embodiments, a suitable growth medium for higher plants can include any growth medium for plants, including, but not limited to, soil, sand, any other particulate media that support root growth (e.g., vermiculite, perlite, etc.) or hydroponic culture, as well as suitable light, water and nutritional supplements which optimize the growth of the higher plant.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

In embodiments, the present disclosure relates to regenerable cells for use in tissue culture of. The tissue culture will preferably be capable of regenerating plants having the physiological and morphological characteristics of the foregoing plants and of regenerating plants having substantially the same genotype as the foregoing plants. Preferably, the regenerable cells in such tissue cultures will be embryos, protoplasts, meristematic cells, callus, pollen, leaves, anthers, roots, root tips, flowers, seeds, pods or stems. Still further, embodiments of the present disclosure relate to plants regenerated from the tissue cultures of embodiments of the disclosure.

In an aspect of the subject disclosure, the methods provided are applicable on a wide variety of plants and plant cell systems. In embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea mays.*

The following examples are provided to illustrate certain particular features and/or embodiments. The examples should not be construed to limit the disclosure to the particular features or embodiments exemplified.

EXAMPLES

Example 1: Design of Gene Expression Construct

Figure 1:
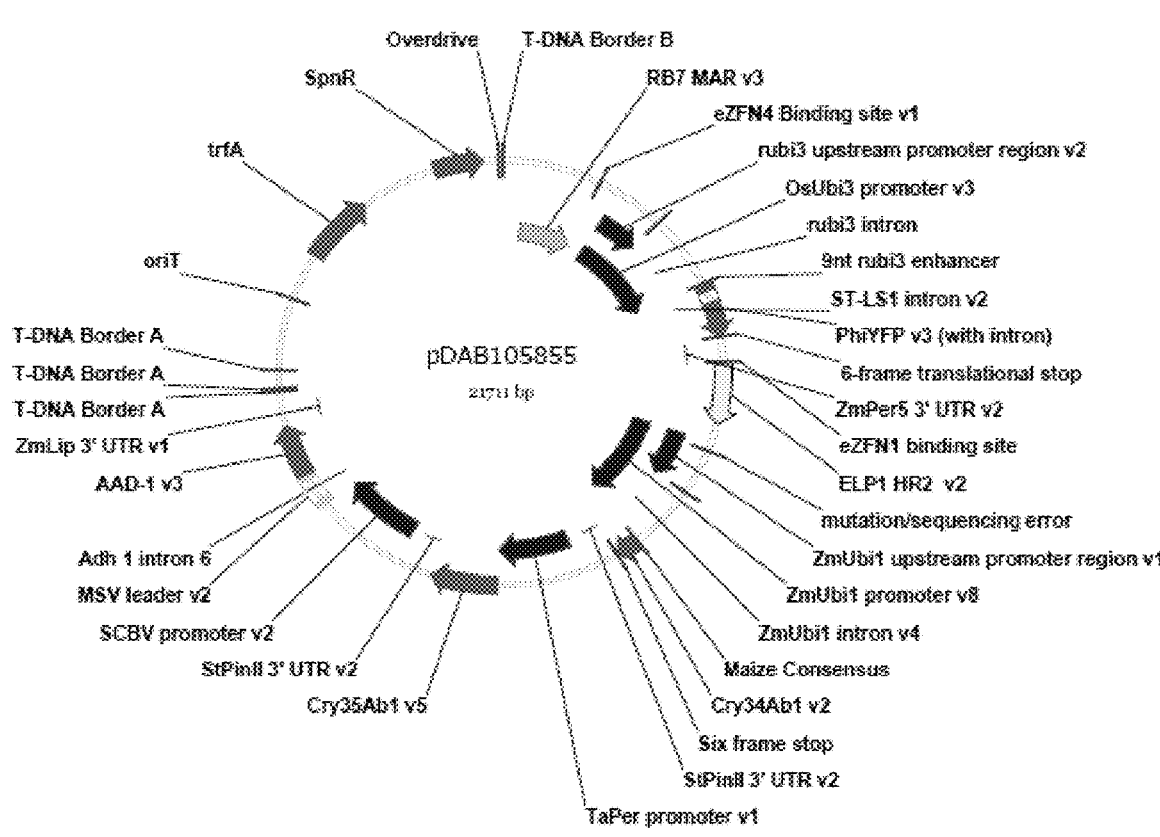
FIG. 1: This figure shows a plasmid map of pDAB105855 containing target DNA sequence comprising: RB7 MAR sequence/eZFN4 Binding site v1, OsUbi3 promoter/Phi YFP/ZmPer5 3'UTR v2/eZFN1 binding site/ELP1 HR2 v2, ZmUbi1 promoter v8/Cry34Ab1 v2/StPinII 3' UTR v2, TaPer promoter v3/Cry35Ab1 v5/StPinII 3' UTR v2, SCBVv2/AAD-1v3/ZmLip 3' UTR v1 between T-DNA borders.

The Engineered Transgene Integration Platform (ETIP) was previously described in U.S. Patent Application No. 20140090113A1, herein incorporated by reference in its entirety. The ETIP contains an engineered landing pad sequence, several engineered zinc finger binding sites (eZFN), and gene expression cassettes as shown in the binary plasmid vector pDAB105855 (FIG. 1; SEQ ID NO:1). As described in U.S. Patent Application No. 20140090113A1, the binary plasmid, pDAB105855, was transformed and integrated into the genome of *Zea mays* c.v. B104 (see, Example 8 of U.S. Patent Application No. 20140090113A1). Positive transgenic plants containing full-length, simple insertion events of the pDAB105855 T-strand insert were confirmed via molecular analysis (see, Example 6 of U.S. Patent Application No. 20140090113A1). The transgene expression cassettes within the *Agrobacterium* border regions of pDAB105855 were located within the chromosome of the *Zea mays* c.v. B104 genome as a full length T-strand insert. The resulting transgenic plant containing transgenic event, pDAB105855-#2, was self-pollinated to produce homozygous progeny plants that contained full length copies of the T-strand insert from pDAB105855. These progeny plants were confirmed as being homozygous by molecular confirmation assays.

Example 2: Design of Gene Expression Construct

Figure 2:
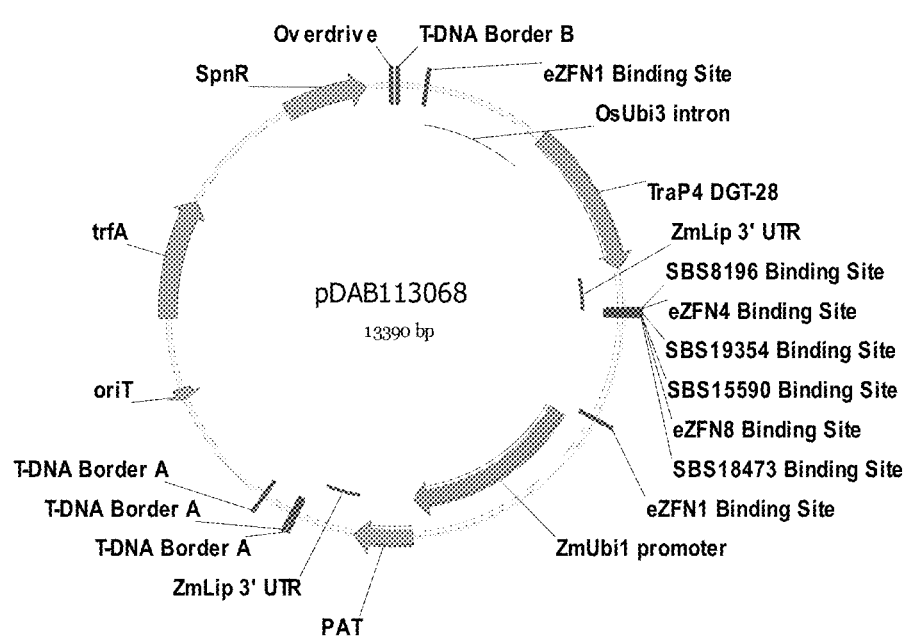
FIG. 2: This figure shows a plasmid map of pDAB113068 containing target DNA sequence comprising: eZFN1 Binding Site; intron from OsUbi3 promoter::TraP4 DGT-28 transgene::ZmLip 3'UTR; SBS8196 Binding Site::eZFN4 Binding Site::SBS19354 Binding Site::SBS15590 Binding Site::eZFN8 Binding Site::SBS18473 Binding Site::eZFN1 Binding Site; ZmUbi1 promoter::PAT transgene::ZmLip 3' between T-DNA borders.

A second gene expression construct containing the dgt-28 transgene and several eZFN binding sites was designed and built. This gene expression construct was labeled as pDAB113068 (FIG. 2; SEQ ID NO:2) and contained the following gene elements: the eZFN1 Binding Site; the Oryza sativa Ubiquitin 3 intron (OsUbi3 intron; Sivamani, E., Qu, R., (2006) Plant Molecular Biology 60; 225-239) driving the expression of the dgt-28 transgene (DGT-28; International Patent Application No. 2013116700) fused with the TraP4 chloroplast transit peptide (International Patent Application No. 2013158766) and terminated by the *Zea mays* lipase 3'UTR (ZmLip 3'UTR; U.S. Pat. No. 7,179,902); a linker region containing multiple site specific nuclease binding sites (SBS8196 Binding Site::eZFN4 Binding Site:: SBS19354 Binding Site::SBS15590 Binding Site::eZFN8 Binding Site::SBS 18473 Binding Site::eZFN1 Binding Site); and, the *Zea mays* Ubiquitin1 promoter (ZmUbi1 promoter; Christensen et al. (1992) *Plant Molecular Biology* 18; 675-689) driving the expression of the pat transgene (PAT; Wohlleben et al. (1988) *Gene* 70(1); 25-37) and terminated by the *Zea mays* lipase 3'UTR. This gene expression construct was transformed into the pDAB105855-#2 event *Zea mays* plants that were previously confirmed to contain homozygous copies of pDAB105855.

Example 3: *Agrobacterium* Strain Production and *Zea mays* Transformation

Inoculation of *Agrobacterium tumefaciens*

The pDAB113068 binary plasmid was transformed into the pDAB105855-#2 event Zea mays plants via an *Agrobacterium* mediated transformation protocol. The binary expression vectors were transformed into *Agrobacterium tumnefaciens* strain EHA105. Bacterial colonies were selected, and binary plasmid DNA was isolated and confirmed via restriction enzyme digestion. The *Agrobacterium* cultures were streaked from glycerol stocks and incubated for growth. On the day of an experiment, the resulting cultures of *Agrobacterium* were used for the transformation of *Zea mays* plants containing the pDAB 105855-#2 event.

Zea mays Transformation

Experimental constructs were transformed into Zea mays plants containing the pDAB105855-#2 event via *Agrobacterium*-mediated transformation of immature embryos isolated from the inbred line, *Zea mays* c.v. B104 plants containing the pDAB105855-#2 event. The method used is similar to those published by Ishida et al. (1996) Nature Biotechnol 14:745-750 and Frame et al. (2006) Plant Cell Rep 25: 1024-1034, but with several modifications and improvements to make the method amenable to high-throughput transformation. An example of a method used to produce a number of transgenic events in *Zea mays* is given in U.S. Patent Application No. 20130157369A1, beginning with the embryo infection and co-cultivation steps.

Example 4: Molecular Confirmation of Copy Number at T0

Putative transgenic *Zea mays* plants were sampled at the V2-3 leaf development stage for transgene presence using a pat transgene quantitative PCR assay. Total DNA was extracted from leaf punches using MagAttract® DNA extraction kit (Qiagen) as per the manufacturer's instruction.

To detect the genes of interest, gene-specific DNA fragments were amplified with TaqMan® primer/probe sets containing a FAM-labeled fluorescent probe for the pat transgene and a HEX-labeled fluorescent probe for an endogenous reference gene control. Next, the PCR reactions were carried out in a final volume of 10 µl reaction containing 5 µl of Roche LightCycler® 480 Probes Master Mix (Roche Applied Sciences, Indianapolis, IN); 0.4 µl each of the primers from 10 µM stocks to a final concentration of 400 nM; 0.4 µl each of the probes from 5 µM stocks to a final concentration of 200 nM, 0.1 µl of 10% polyvinylpyrrolidone (PVP) to final concentration of 0.1%; 2 µl of 10 ng/µl genomic DNA and 0.5 µl water. The DNA was amplified in a Roche LightCycler® 480 System under the following conditions: 1 cycle of 95° C. for 10 min; 40 cycles of the following 3-steps: 95° C. for 10 seconds; 58° C. for 35 seconds and 72° C. for 1 second, and a final cycle of 4° C. for 10 seconds. The pat transgene copy number was determined by comparison of Target (gene of interest)/Reference values for unknown samples (output by the LightCycler® 480) to Target/Reference values of the pat transgene copy number controls. The resulting T0 plants were selfed to obtain T1 seed, which was screened to identify transgenic plants that were homozygous. Zygosity screening was completed on the T1 progeny plants to identify the plants that were homozygous for both the target and donor gene events. These progeny plants were utilized for the additional experiments.

Example 5: Mapping of Chromosomal Location of the Events

The transgenic plant containing target pDAB105822-#2 event, and donor pDAB113068-#250 event were analyzed using Next Generation Sequencing (NGS) to determine the genomic insertion site locations of both transgenes. The sequence reads were aligned to the *Zea mays* B73 reference genome from maizeGDB (Andorf et al. (2015) MaizeGDB 2015: New tools, data, and interface for the maize model organism database. Nucleic Acids Research doi: 10.1093/nar/gkv1007). Target pDAB105822#2 and donor pDAB113068-#250 event were found to be inserted on the same chromosome. The target pDAB105855-#2 event was mapped to Chromosome 5: 188,528,595 . . . 188,528,607, while the donor pDAB113068-#250 event was mapped to Chromosome 5: 147,625,397 . . . 147,625,455.

Example 6: Design of ZFNs and Gene Expression Construct

Zinc finger proteins directed against the eZFN1 DNA sequence which comprise a site specific cleavage site within the T-DNA of pDAB105855 (see, FIG. 1) were designed as previously described. See, e.g., Urnov et al. (2005) Nature 435:646-651. Exemplary recognition helices were previously disclosed as "recognition helix region designs" in U.S. Patent Application No. 20140090113A1 (herein incorporated by reference in its entirety). The target sequence site that the zinc finger recognized and bound is provided in Table 1 as SEQ ID NO:3.

TABLE 1

| Site specific nuclease target sequence | | |
|---|---|---|
| Site Name | SEQ ID NO: | Target Sequence |
| eZFN1 Binding Site | 3 | caatcctgtccctagtggataaactgcaaaaggc |

45

The site specific nuclease zinc finger designs were incorporated into vectors encoding a protein having at least one finger with a CCHC structure. See, U.S. Patent Application No. 20080182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al. (1998) Proc. Natl. Acad. Sci. USA 95:10564-10569) via a four amino acid ZC linker and an opaque-2 nuclear localization signal derived from *Zea mays* to form eZFN1 specific zinc-finger nucleases (ZFNs). Expression of the fusion proteins in a bicistronic expression construct utilizing a 2A ribosomal stuttering signal as described in Shukla et al. (2009) *Nature* 459:437-441 was driven by a relatively strong, constitutive *Zea mays* Ubiquitin 1 promoter.

The optimal zinc fingers were verified for cleavage activity using a budding yeast based system previously shown to identify active nucleases. See, e.g., U.S. Patent Publication No. 20090111119; Doyon et al. (2008) *Nat Biotechnol.* 26:702-708; Geurts et al. (2009) *Science* 325:433. Zinc fingers for the various functional domains were selected for in-vivo use. Of the numerous ZFNs that were designed, produced and tested to bind to the putative eZFN1 polynucleotide target sites, a pair of ZFNs were identified as having in vivo activity at high levels, and selected for further experimentation. These ZFNs were characterized as being capable of efficiently binding and cleaving the site specific eZFN1 genomic polynucleotide target sites in planta. After testing the ZFN pairs in the budding yeast assay, ZFN pairs which optimally bound the eZFN1 binding site were advanced for testing in *Zea mays*.

Zinc finger nuclease constructs for expression in *Zea mays*;

Plasmid vectors containing ZFN expression constructs of the exemplary zinc finger nucleases, which were identified using the yeast assay and described above, were designed and completed using skills and techniques commonly known in the art. Each zinc finger-encoding sequence was fused to a sequence encoding an opaque-2 nuclear localization signal (Maddaloni et al. (1989) *Nuc. Acids Res.* 17(18):7532), that was positioned upstream of the zinc finger nuclease.

Figure 3:
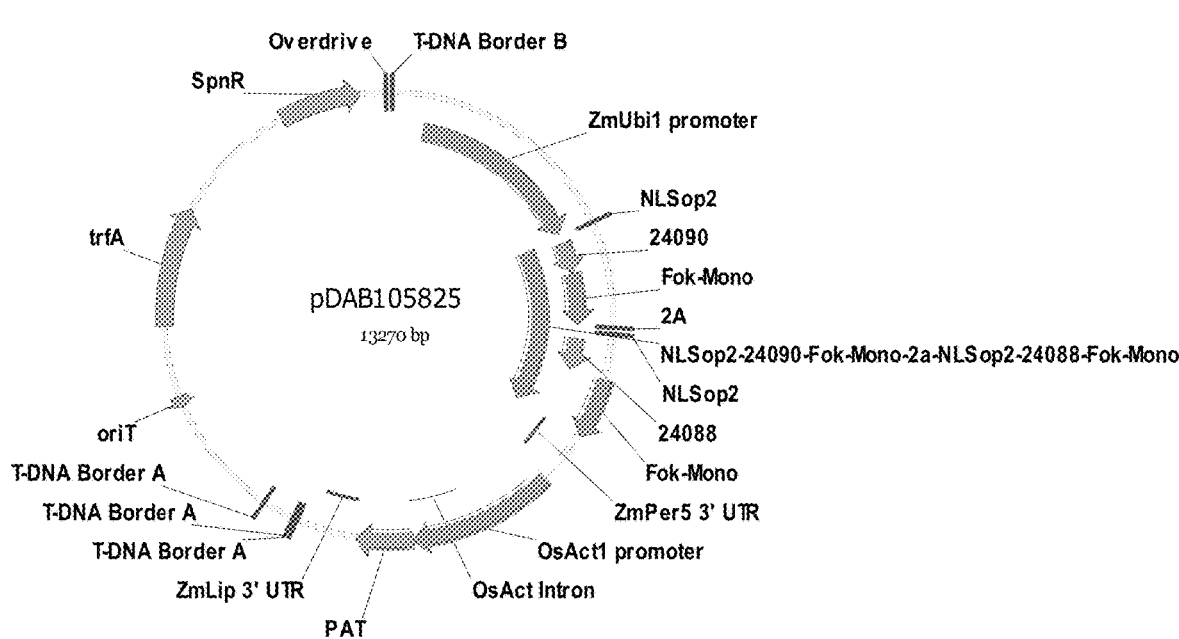
FIG. 3: This figure shows a plasmid map of pDAB105825 containing the expression cassette for eZFN1 site specific nuclease.

Next, the opaque-2 nuclear localization signal::zinc finger nuclease fusion sequence was paired with the complementary opaque-2 nuclear localization signal::zinc finger nuclease fusion sequence. As such, each construct consisted of a single open reading frame comprised of two opaque-2 nuclear localization signal::zinc finger nuclease fusion sequences separated by the 2A sequence from *Thosea asigna* virus (Mattion et al. (1996) *J. Virol.* 70:8124-8127). Expression of the ZFN coding sequence was driven by the highly expressing constitutive *Zea mays* Ubiquitin 1 Promoter (Christensen et al. (1992) Plant Mol. Biol. 18(4):675-89) and flanked by the *Zea mays* Per 5 3' polyA untranslated region (U.S. Pat. No. 6,699,984). The resulting four plasmid constructs were confirmed via restriction enzyme digestion and via DNA sequencing. FIG. 3 provides a graphical representation of the completed plasmid construct of pDAB105825. The ZFN expressed in plasmid construct, pDAB105825, contains "Fok-Mono" which is a wildtype FokI endonuclease.

Example 7: *Zea mays* Transformation

The resulting zinc finger nuclease construct, pDAB105825, was transformed into *Zea mays* c.v. B104 plants using the methods previously described in Example 3 above. The resulting transgenic plant containing was self-pollinated to produce homozygous progeny plants that contained full length copies of the T-strand insert from pDAB105825. These progeny plants were confirmed as being homozygous by molecular confirmation assays as described in Example 4 above.

Example 8: Crossing of the Homozygous T1 Plants for Producing an F1 Population The T1 pDAB105825 events were screened for zygosity and expression of the aad-1 transgene. Based on these results, homozygous T1 plants from one pDAB105825 event were selected for crossing with pDAB105855/pDAB113068 plant events to produce F1 progeny plants. Reciprocal crosses were made so that parents were both male and female. The plants were crossed by hand; pollen from the anthers of a mature male parent was introduced to the stigma of the mature female parent. Plants ready for crossing were removed from the other plants to reduce the likelihood that unintended pollen would fertilize the female maize plants. Female plants were emasculated (anthers removed prior to dehiscence) by detasseling. The anthers from the male parent were totally removed from the male plant, and the pollen was isolated from the anthers and used to fertilize the emasculated female. The isolated pollen was rubbed onto the receptive silks of female plants, coating the silks to reduce the chance of any unintended pollinations. The seed from the fertilized plants was collected and sewn into soil. The resulting F1 populations were grown in the greenhouse under standard maize growing conditions.

Figure 4:
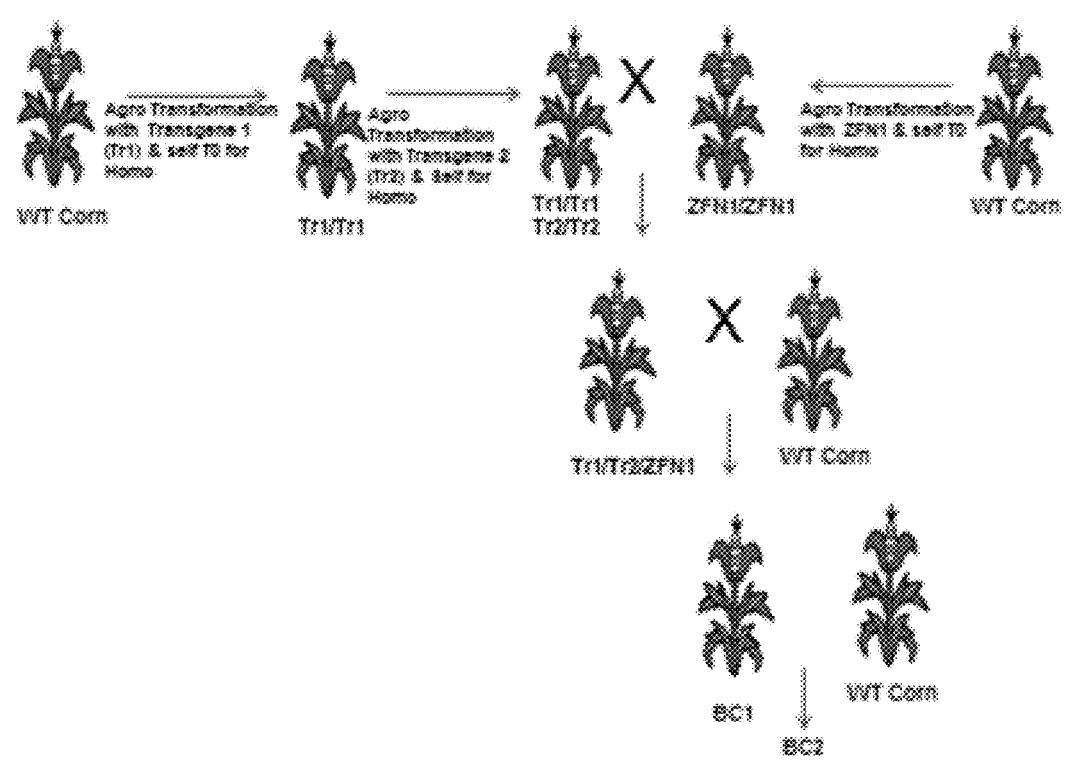
FIG. 4: This figure shows the transformation and breeding strategy used to exemplify the increased recombination frequencies between two alleles resulting from the cleavage of one of two homologous chromosomes by a site specific nuclease (e.g., a zinc finger nuclease).

Example 9: Crossing of the F1 Plants to Sibling Null Plants to Produce a BC1 Population The resulting F1 progeny plants that contained all three events (i.e., pDAB105855/pDAB113068/pDAB105825) were grown to maturity and backcrossed to sibling null parent plants to produce a BC1 population. The crossing strategy is set forth below and diagrammed in FIG. 4. The resulting BC1 populations were molecularly characterized to calculate the recombination frequencies which occurred between the genetically linked transgenes between the pDAB105855 gene and the pDAB113068 gene. As a result of cleaving one of two homologous chromosomes with zinc finger nucleases, it was hypothesized that the recombination frequency between the pDAB 105855 gene and the pDAB113068 gene would increase as the result of the introduction of a double strand break at the eZFN1 binding site by a zinc finger nuclease FIG. 5.

Example 10: Crossing of the BC1 Plants to Sibling Null Plants to Produce a BC2 Population The resulting BC1 progeny plants that contained all three events (i.e., pDAB105855/pDAB113068/pDAB105825) were grown to maturity and backcrossed to sibling null parent plants to produce a BC2 population. The crossing strategy is set forth below and diagrammed in FIG. 4. The resulting BC2 populations were molecularly characterized to calculate the recombination frequencies which occurred between the genetically linked transgenes; the pDAB105855 gene and the pDAB113068 gene. As a result of cleaving one of two homologous chromosomes with zinc finger nucleases, it was hypothesized that the recombination frequency between the pDAB105855 gene and the pDAB113068 gene would increase as the result of the introduction of a double strand break at the eZFN1 binding site by a zinc finger nuclease FIG. 5.

Example 11: Calculation of the Percentage of Recombination Frequency

The recombination frequency between the genetically linked transgenes, for instance the pDAB105855 gene and the pDAB113068 gene, was calculated and is provided in Table 2. Gene 1 and 2 are genetically linked and therefore frequently co-segregate. The percentage of recombination frequency was determined by dividing the number of recombinant offspring (containing gene 1 or gene 2 alone) by the total number of offspring observed.

The control progeny plants, which did not include the introduction of a zinc finger nuclease within the plant crossing experiments resulted in a low percentage of recombination between the pDAB105855 gene and the pDAB113068 gene was calculated at 3.5%. These control plants did not contain a double strand break between the genetically linked transgenes the pDAB105855 gene and the pDAB113068 gene and any segregation occurring between the pDAB105855 gene and the pDAB113068 gene resulted from natural cell processes occurring during the various cell cycles and plant development phases.

Comparatively, the recombination frequency increased by up to 62.3% in the experimental progeny plants, and the recombination frequency ranged from 4.4% to 62.3%. The experimental progeny plants, which included the introduction of a zinc finger nuclease within the plant crossing experiments resulted in a higher percentage of recombination between the pDAB105855 gene and the pDAB113068 gene was calculated was much greater than 3.5% recombination frequency of the control plants. These experimental plants did contain a double strand break between the genetically linked transgenes of the pDAB105855 gene and the pDAB113068 gene, and the increase in segregation occurring between the pDAB 105855 gene and the pDAB113068 gene resulted from the introduction of the double strand break. The frequency of recombinant offspring was increased dramatically (up to 62%) with the introduction of a ZFN and the induction of targeted double strand break at a binding site located between two genetically linked genes; the pDAB 105855 gene and the pDAB113068 gene.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

TABLE 2

Recombination Frequency in Progeny Plants after Crossing Between Parental Plants to Introduce a Double Strand Break Between Genetically Linked Genes.

| Cross/ Generation | Total Offspring | Null/ pDAB105825 | pDAB105855/ pDAB113068/ pDAB105825 | pDAB113068/ pDAB105825 | pDAB10585/ pDAB105825 | Recombinant Offspring | Percentage of Recombination |
|---|---|---|---|---|---|---|---|
| Control BC1 | 57 | 35 | 20 | 1 | 1 | 2 | 3.5% |
| 1ZFN BC1 | 68 | 62 | 3 | 2 | 1 | 3 | 4.4% |
| 1ZFN BC2 | 61 | 29 | 25 | 3 | 4 | 7 | 11.5% |
| 2ZFN BC1 | 70 | 31 | 34 | 4 | 1 | 5 | 7.1% |
| 2ZFN BC2 | 68 | 37 | 28 | 3 | 0 | 3 | 4.4% |
| 3ZFN BC1 | 53 | 28 | 9 | 0 | 16 | 16 | 30.2% |
| 3ZFN BC2 | 63 | 29 | 28 | 4 | 1 | 5 | 7.9% |
| 4ZFN BC1 | 69 | 26 | 0 | 0 | 43 | 43 | 62.3% |
| 4ZFN BC2 | 57 | 31 | 0 | 0 | 26 | 26 | 45.6% |
| 5ZFN BC1 | 69 | 23 | 41 | 2 | 3 | 5 | 7.2% |
| 5ZFN BC2 | 72 | 21 | 31 | 12 | 8 | 20 | 27.8% |

What is claimed is:

1. A method for increasing the frequency of genetic recombination between a first locus genetically linked to a second locus within a genome of a plant, the method comprising the steps of:

a) introducing a site specific nuclease into the genome of the plant;

b) producing a double stranded break at a genomic target site with the site specific nuclease in one of two homologous chromosomes, wherein the double stranded break is produced by a site specific nuclease in one of two homologous chromosomes, and a double stranded break is not produced in the second homologous chromosome;

c) undergoing recombination within the plant genome; and, d) modifying the plant genome, wherein the modified plant genome comprises increased frequency of genetic recombination between the first locus and the second locus to reduce the genetic linkage between the first locus and the second locus.

2. The method of claim 1, wherein the first locus encodes a trait and the second locus encodes a different trait.

3. The method of claim 1, wherein recombination comprises meiotic recombination or mitotic recombination.

4. The method of claim 1, wherein the increased frequency of genetic recombination ranges from 1.25 to 17.8 fold.

5. The method of claim 1, wherein the distance from the first locus to the second locus ranges from about 0.01 CM to about 500 CM.

6. The method of claim 1, wherein the distance from the first locus to the second locus ranges from about 10 bp to about 10 Mbp.

7. The method of claim 1, wherein the first locus is located on a first chromosome, and the second locus is located on a second chromosome.

8. The method of claim 1, wherein the first locus and the second locus are present in a genomic location with low levels of recombination frequency.

9. The method of claim 2, wherein the trait comprises a desirable trait or an undesirable trait.

10. The method of claim 9, wherein the desirable trait or the undesirable trait is either a native trait or a transgenic trait.

11. The method of claim 10, wherein the undesirable trait is selected from the group consisting of reduced yield, reduced resistance to disease, reduced resistance to pests, reduced tolerance to herbicide tolerance, reduced growth, reduced size, reduced production of biomass, reduced amount of produced seeds, reduced resistance against salinity, reduced resistance against heat stress, reduced resistance against cold stress, reduced resistance against drought stress, and any combination thereof.

12. The method of claim 10, wherein the desirable trait is selected from the group consisting of increased yield, increased resistance to disease, increased resistance to pests, increased tolerance to herbicides, increased growth, increased size, increased production of biomass, increased amount of produced seeds, increased resistance against salinity, increased resistance against heat stress, increased resistance against cold stress, increased resistance against drought stress, and any combination thereof.

13. The method of claim 1, wherein the first locus comprises a polymorphic marker and the second locus comprise a trait.

14. The method of claim 1, wherein the first locus comprises a polymorphic marker and the second locus comprises a polymorphic marker.

15. The method of claim 1, wherein the site specific nuclease is selected from the group consisting of a zinc finger nuclease, a TALEN nuclease, a CRISPR nuclease, a meganuclease, and a leucine zipper nuclease.

16. The method of claim 1, wherein the site specific nuclease is delivered to a cell by intragenomic recombination or via direct delivery.

17. The method of claim 1, wherein the genome of the plant is a polyploid.

18. The method of claim 1, the method further comprising the steps of:

e) producing a progeny plant comprising the modified plant genome;

f) crossing the progeny plant with another plant or to itself; and, g) generating a seed from the progeny plant.

19. The method of claim 2, wherein the first locus comprising a first trait is located on the first homologous chromosome and the second locus comprising a second trait is located on the first homologous chromosome.

20. The method of claim 8, wherein the resulting double strand break occurs between the first locus comprising the first trait and the second locus comprising the second trait, thereby resulting in a progeny plant comprising only the first locus comprising the first trait.

21. The method of claim 2, wherein the first trait is either a recessive or a dominant trait.

22. The method of claim 2, wherein the first trait is either a heterozygous or a homozygous trait.

23. The method of claim 1, wherein the plant is selected from a dicotyledonous plant or a monocotyledonous plant.

24. The method of claim 23, wherein the plant is selected from the group consisting of a tobacco plant, a soybean plant, a cotton plant, a *Brassica* plant, a corn plant, a sorghum plant, a wheat plant, and a rice plant.

* * * * *

SEQUENCE LISTING

```
Sequence total quantity: 3
SEQ ID NO: 1              moltype = DNA  length = 15950
FEATURE                  Location/Qualifiers
misc_feature             1..15950
                         note = Gene expression cassetted from pDAB105855
source                   1..15950
                         mol_type = other DNA
                         organism = synthetic construct
SEQUENCE: 1
cagtcagcat catcacacca aaagttaggc ccgaatagtt tgaaattaga aagctcgcaa   60
ttgaggtcta caggccaaat tcgctcttag ccgtacaata ttactcacca gatcctaacc  120
ggtgtgatca tgggccgcga ttaaaaatct caattatatt tggtctaatt tagtttggta  180
ttgagtaaaa caaattcggc gccatgcccg ggcaagcggc cgcacaagtt tgtacaaaaa  240
agcaggctga gtattcacta cagtagtgca tcgatggagt catcacgcag actatctcag  300
catgtgcgta gcacgtctag acctaggtag gttaattaag cttgcatgcc tgcagatccc  360
cggggatctc cgccgattaa aaatctcaat tatatttggt ctaatttagt ttggtattga  420
gtaaaacaaa ttcgaaccaa accaaaatat aaatatatag tttttatata tatgccttta  480
agacttttta tagaattttc tttaaaaaat atctagaaat atttgcgact cttctggcat  540
gtaatatttc gttaaatatg aagtgctcca tttttattaa ctttaaataa ttggttgtac  600
gatcactttc ttatcaagtg ttactaaaat gcgtcaatct ctttgttctt ccatattcat  660
```

-continued

```
atgtcaaaac ctatcaaaat tcttatatat ctttttcgaa tttgaagtga aatttcgata   720
atttaaaatt aaatagaaca tatcattatt taggtatcat attgattttt atacttaatt   780
actaaatttg gttaactttg aaagtgtaca tcaacgaaaa attagtcaaa cgactaaaat   840
aaataaatat catgtgttat taagaaaatt ctcctataag aatattttaa tagatcatat   900
gtttgtaaaa aaaattaatt tttactaaca catatattta cttatcaaaa atttgacaaa   960
gtaagattaa aataatattc atctaacaaa aaaaaaacca gaaaatgctg aaaacccggc  1020
aaaaccgaac caatccaaac cgatatagtt ggtttggttt gattttgata taaaccgaac  1080
caactcggtc catttgcacc cctaatcata atagctttaa tatttcaaga tattattaag  1140
ttaacgttgt caatatcctg gaaattttgc aaaatgaatc aagcctatat ggctgtaata  1200
tgaatttaaa agcagctcga tgtggtggta atatgtaatt tacttgattc taaaaaaata  1260
tcccaagtat taataatttc tgctaggaag aaggttagct acgatttaca gcaaagccag  1320
aatacaatga accataaagt gattgaagct cgaaatatac gaaggaacaa atattttaa   1380
aaaaatacgc aatgacttgg aacaaaagaa agtgatatat tttttgttct taaacaagca  1440
tcccctctaa agaatggcag ttttcctttg catgtaacta ttatgctccc ttcgttacaa  1500
aaattttgga ctactattgg gaacttcttc tgaaaatagc acttgtcccg ggcatagaga  1560
taaactgcaa aaggcccttg gccacggtgg ccagatccac tagaggcgcg cctctagtgc  1620
ggccgcttaa ttaacttact agtgctagcc tcgaggtcga catttaaatg atgagtgata  1680
ctcaggactc aggactcact ctgctgatcg tccaacaggc ttcgcgatga gtcggacaac  1740
tttgtataca aaagttgaat atgtgtatct aactcacgac gcactcagca actcatccag  1800
tcaagttcga gtcagtgagt tggtctagac ctaggtaggt taattaagct tgcatgcctg  1860
cagatccccg gggatctccg cgatgtgaag aacaggtaaa tcacgcagaa gaacccatct  1920
ctgatagcag ctatcgatta gaacaacgaa tccatattgg gtccgtggga aatacttact  1980
gcacaggaag ggggcgatct gacgaggccc cgccaccggc ctcgacccga ggccgaggcc  2040
gacgaagcgc cggcgagtac ggcgccgcgg cggcctctgc ccgtgccctc tgcgcgtggg  2100
agggagaggc cgcggtggtg ggggcgcgcg cgcgcgcgcg cgcagctggt gcggcggcgc  2160
gggggtcagc cgccgagccg aggagcaggg aggagcaggg gcgcgtggac gcgaacttcc  2220
gatcggttgg tcagagtgcg cgagttgggc ttagccaatt aggtctcaac aatctattgg  2280
gccgtaaaat tcatgggccc tggtttgtct aggcccaata tcccgttcat ttcagcccac  2340
aaatatttcc ccagaggatt attaaggccc acacgcagct tatagcagat caagtacgat  2400
gtttcctgat cgttggatcg gaaacgtacg gtcttgatca ggcatgccga cttcgtcaaa  2460
gagaggcggc atgacctgac gcggagttgg ttccgggcac cgtctggatg gtcgtaccgg  2520
gaccggacac gtgtcgcgcc tccaactaca tggacacgtg tggtgctgcc attgggccgt  2580
acgcgtggcg gtgaccgcac cggatgctgc ctcgcaccgc cttgcccacg ctttatatag  2640
agaggttttc tctccattaa tcgcatagcg agtcgaatcg accgaagggg aggggagcg   2700
aagctttgcg ttctctaatc gcctcgtcaa ggtaactaat caatcacctc gtcctaatcc  2760
tcgaatctct cgtggtgccc gtctaatctc gcgattttga tgctcgtggt ggaaagcgta  2820
ggaggatccc gtgcgagtta gtctcaatct ctcagggttt cgtgcgattt tagggtgatc  2880
cacctcttaa tcgagttacg gtttcgtgcg attttagggt aatcctctta atctctcatt  2940
gatttagggt ttcgtgagaa tcgaggtagg gatctgtgtt atttatatcg atctaataga  3000
tggattggtt ttgagattgt tctgtcagat ggggattgtt tcgatatatt accctaatga  3060
tgtgtcagat ggggattgtt tcgatatatt accctaatga tgtgtcagat ggggattgtt  3120
tcgatatatt accctaatga tggataataa gagtagttca cagttatgtt ttgatcctgc  3180
cacatagttt gagtttttgtg atcagattta gtttcactta tttgtgctta gttcggatgg  3240
gattgttctg atattgttcc aatagatgaa tagctcgtta ggttaaaatc tttaggttga  3300
gttaggcgac acatagttta tttcctctgg atttggattg gaattgtgtt cttagttttt  3360
ttcccctgga tttggattgg aattgtgtgg agctgggtta gagaattaca tctgtatcgt  3420
gtacacctac ttgaactgta gagctgggt tctaaggtca atttaatctg tattgtatct  3480
ggctctttgc ctagttgaac tgtagtgctg atgttgtact gtgtttttttt acccgtttta  3540
tttgctttac tcgtgcaaat caaatctgtc agatgctaga actaggtggc tttattctgt  3600
gttcttacat agatctgttg tcctgtagtt acttatgtca gtttttgttat tatctgaaga  3660
tattttttggt tgttgcttgt tgatgtggtg tgagctgtga gcagcgctct tatgattaat  3720
gatgctgtcc aattgtagtg taatatgatg tgattgatat gttcatctat tttgagctga  3780
cagtaccgat atcgtaggat ctggtgccaa cttattctcc agctgcttt ttttacctat   3840
gttaattcca atcctttctt gcctcttcca gatccagata ccacacgaca ccatgtcatc  3900
tggagcactt ctctttcatg ggaagattcc ttacgttgtg gagatggaag ggaatgttga  3960
tggccacacc tttagcatac gtgggaaagg ctacggagat gcctcagtgg gaaaggtatg  4020
tttctgcttc tacctttgat atatatataa taattatcac taattagtag taatatagta  4080
tttcaagtat tttttttcaaa ataaaagaat gtagtatata gctattgctt ttctgtagtt  4140
tataagtgtg tatattttaa tttataactt ttctaatata tgaccaaaac atggtgatgt  4200
gcaggttgat gcacaattca tctgtactac cggagatgtt cctgtgcctt ggagcacact  4260
tgtcaccact ctcacctatg gagcacagtc ctttgccaag tatggtccag agttgaagga  4320
cttctacaag tcctgtatgc cagatggcta tgtgcaagag cgcacaatca cctttgaagg  4380
agatggcaac ttcaagacta gggctgaagt cacctttgag aatgggtctg tctacaatag  4440
ggtcaaactc aatggtcaag gcttcaagaa agatggtcac gttgtgggaa agaacttgga  4500
gttcaacttc actccccact gcctctacat ctggggagac caagccaacc acggtctcaa  4560
gtcagccttc aagatatgtc atgagattac tggcagcaaa ggcgacttca gtagtggctga  4620
ccacacccag atgaacactc ccattggtgg aggtccagtt catgttccag agtatcatca  4680
tatgtcttac catgtgaaac tttccaaaga tgtgacagac cacagagaca catgagctct  4740
gaaagaaact gtcagagctg ttgactgtcg caagacctac ctttgagtag ttagcttaat  4800
cacctagagc tcggtaacct ttaaactgag ggcactgaag tcgcttgatg tgctgaattg  4860
tttgtgatgt tggtggcgta ttttgtttaa ataagtaagc atggctgtga ttttatcata  4920
tgatcgatct ttggggtttt atttaacaca ttgtaaaatg tgtatctatt aataactcaa  4980
tgtataagat gtgttcattc ttcggttgcc atagatctgc ttatttgacc tgtgatgttt  5040
tgactccaaa aaccaaaatc aacaatcaat aaactatgga aatatgtcca cctgttttct  5100
gaagagttca tctaccattc cagttggcat ttatcagtgt tgcagcggcg ctgtgctttg  5160
taacataaca attgttacgg catatatcca acaatcctgt ccctagtgga taaactgcaa  5220
aaggcccaga tctggttaat gagggaaagt aatctcacaga agtacagtcc cctctgaaag  5280
gaacatggct tatactccat gccttcaagt agatttgaag tcattgcttc acttaggaag  5340
ttctattgtt tgagatggtg gttatgacag gctccgttta aacttgctgg tgttatgtgc  5400
```

-continued

```
ccttgaagta gccaggaggt ttgttgttcc catacaccca tgagggcttg gtcagttttc   5460
tctggtatgt tactggatgg agagggtctc caagtgtgca atgtgaactt aacaacatcc   5520
caggcactc  acccctcact gacttttttg gctactaata aacagactag ctatcattca   5580
cctttgtagc cagaatccca ggggatctgc acccagtact cattccagct tgcagaataa   5640
tatccaccag gtcatgtaat aagaggagtc aaggacttag tcttgtttcc tcactcatca   5700
attatgaggt attgccatga tgcctagcca cctcacacaa cctagacaag gccactgtgt   5760
ccaagactca ttcacccagt cactagcacc cagtcttgca cccaggggg  ttctggaggc   5820
cctccaaata ctaagtaaca tttttccagg cacacaatgt gtgagtagga cacagtgcag   5880
ttgatcaaac ccaggtttct tgtgtagtgc cttccctatt gaggaccagg gagcatgccc   5940
acctctcaaa gtcagctctc atcaatctct caacaaactg tttacatatt atctctgatt   6000
cccaggagga ctcagcccca caacttccca tttcaggtat cccttggcat cctagcccta   6060
atgcccattt gttaatatgg gatggctcac ctctgaggac tctagttaca gggtggagtc   6120
tcccttggga tttcagttgg taggttaaaa atgggagtgg catggagagg aaataacaga   6180
ggccctccag caatagcttc tctgtgatga taacccctat actctatatt ttaccttggc   6240
cacggtggcc agatccacta gaggcgcgcc tctagtgcgg ccgcttaatt aacttactag   6300
tgctagcctc gaggtcgacg atatcgcgat cgctctgacc tgaccactag acctgagtga   6360
gtacagatgt gctcggaatc ctgtatattc cgcatcgaac aactttttcta tacaaagttg   6420
ccatgtttaa tacaactcac gactatacta ggcactgagt gactcactga cctgactgag   6480
tgactgtcta gacctaggta ggttaattaa gcttgcatgc ctgcagatcc ccggggatct   6540
ccgcgtgcag cgtgacccgg tcgtgcccct ctctagagat aatgagcatt gcatgtctaa   6600
gttataaaaa attaccacat attttttttg tcacacttgt ttgaagtgca gtttatctat   6660
ctttatacat atatttaaac tttactctac gaataatata atctatagta ctacaataat   6720
atcagtgttt tagagaatca tataaatgaa cagttagaca tggtctaaag gacaattgag   6780
tattttgaca acaggactct acagtttttat ctttttagtg tgcatgtgtt ctcctttttt   6840
tttgcaaata gcttcaccta tataatactt catccatttt attagtacat ccatttaggg   6900
tttagggtta atggttttta tagactaatt tttttagtac atctattta ttctatttta    6960
gcctctaaat taagaaaact aaaactctat tttagttttt ttatttaata atttagatat   7020
aaaatagaat aaaataaagt gactaaaaat taaacaaata cccttttaaga aattaaaaaa   7080
actaaggaaa cattttttctt gtttcgagta gataatgcca gcctgttaaa cgccgtcgac   7140
gagtctaacg gacaccaacc agcgaaccag cagcgtcgcg tcgggccaag cgaagcagac   7200
ggcacggcat ctctgtcgct gcctctggac ccctctcgag agttccgctc caccgttgga   7260
cttgctccgc tgtcggcatc cagaaattgc gtggcggagc ggcagacgtg agccggcacg   7320
gcaggcggcc tcctcctcct ctcacggcac ggcagctacg ggggattcct ttcccaccgc   7380
tccttcgctt tcccttcctc gcccgccgta ataaatagac accccctcca caccctcttt   7440
ccccaacctc gtgttgttcg gagcgcacac acacacaacc agatctcccc caaatccacc   7500
cgtcggcacc tccgcttcaa ggtacgccgc tcgtcctccc cccccccccc tctctacctt   7560
ctctagatcg gcgttccggt ccatggttag ggcccggtag ttctacttct gttcatgttt   7620
gtgttagatc cgtgtttgtg ttagatccgt gctgctagcg ttcgtacacg gatgcgacct   7680
gtacgtcaga cacgttctga ttgctaactt gccagtgttt ctctttgggg aatcctggga   7740
tggctctagc cgttccgcag acgggatcga tttcatgatt ttttttgttt cgttgcatag   7800
ggtttggttt gcccttttcc tttatttcaa tatatgccgt gcacttgttt gtcgggtcat   7860
cttttcatgc tttttttttgt cttggttgtg atgatgtggt ctggttgggc ggtcgttcta   7920
gatcggagta gaattctgtt tcaaactacc tggtggattt attaattttg gatctgtatg   7980
tgtgtgccat acatattcat agttacgaat tgaagatgat ggatggaaat atcgatctag   8040
gataggtata catgttgatg cgggtttac tgatgcatat acagagatgc tttttgttcg    8100
cttggttgtg atgatgtggt gtggttgggc ggtcgttcat tcgttctaga tcggagtaga   8160
atactgtttc aaactacctg tgtatttat taattttgga actgtatgtg tgtgtcatac     8220
atcttcatag ttacgagttt aagatggatg gaaatatcga tctaggatag gtatacatgt   8280
tgatgtgggt tttactgatg catatacatg atggcatatg cagcatctat tcatatgctc   8340
taaccttgag tacctatcta ttataataaa caagtatgtt ttataattat tttgatcttg   8400
atatacttgg atgatggcat atgcagcagc tatatgtgga ttttttttago cctgccttca   8460
tacgctattt atttgcttgg tactgtttct tttgtcgatg ctcaccctgt tgtttggtgt   8520
tacttctgca gccacacgac accatgtccg cccgcgaggt gcacatcgac gtgaacaaca   8580
agaccggcca caccctccag ctggaggaca agaccaagct cgacggcggc aggtggcgca   8640
cctccccgac caacgtggcc aacgaccaga tcaagacctt cgtggccgaa tccaacggct   8700
tcatgaccgg caccgagggc accatctact actccatcaa cggcgaggcc gagatcagcc   8760
tctacttcga caacccgttc gccggctcca acaaatacga cggccactcc aacaagtccc   8820
agtacgagat catcacccag ggcggctccg gcaaccagtc ccacgtgacc tacaccatcc   8880
agaccacctc ctcccgctac ggccacaagt cctgagtagt tagcttaatc acctagaacc   8940
tagacttgtc catcttctgg attggccaac ttaattaatg tatgaaataa aaggatgcac   9000
acatagtgac atgctaatca ctataatgtg ggcatcaaag ttgtgtgtta tgtgtaatta   9060
ctagttatct gaataaaaga gaaagagatc atccatattt cttatcctaa atgaatgtca   9120
cgtgtcttta taattctttg atgaaccaga tgcatttcat taaccaaatc catatacata   9180
taaatattaa tcatatataa ttaatatcaa ttgggttagc aaaacaaatc tagtctaggt   9240
gtgttttgcc cttggccacg gtggccagat ccactagagg cgcgcctcta gtgcggccgc   9300
ttaattaact tactagtgct agcctcgagg tcgactcacg agtggatgac tgtcacgact   9360
gactcatgac tgacttgggc acctcgcgcg cgatgagtat cacaactttg tataataaag   9420
ttgtatcgct ggacgccgta ctgcatcgac ctaggcgagt catgagtcgt cacatgacgt   9480
catgctcatc agacttctag acctaggtag gttaattaag cttgcatgcc tgcagatccc   9540
cggggatctc cgcgcatgaa agaaactgtc gcactgctag accgcacctt gtcactttca   9600
tcgaacacga cctgtgccca agatgacggt gctgcggtct aagtgaggct gaattgcctt   9660
ggacagaagc ggactcccta caattagtta ggccaaacgg tgcatccatg tgtagctccg   9720
ggctcgggct gtatcgccat ctgcaatagc atccatggag ctcgttccat gtagttggag   9780
atgaaccaat gatcgggcgt gtggacgtat gttcctgtct actccgatag tagagtacgt   9840
gttagctctt tcatggtgca agtgaaattt gtgttggttt aattacccct acgttagttg   9900
cgggacagga gacacatcat gaatttaaag gcgatgatgt cctctcctgt aatgttattc   9960
ttttgatgtg atgaatcaaa atgtcatata aaacatttgt tgctctttag ttaggcctga   10020
tcgtagaacg aaatgctcgt gtagcggggc tacgagccta tgacgcaata acactggttt   10080
gccggcccgg agtcgcttga caaaaaaaag catgttaagt ttatttacaa ttcaaaacct   10140
```

-continued

```
aacatattat attccctcaa agcaggttca cgatcacacc tgtacctaaa aaaaacatga   10200
agaatatatt actccattat tatgagatga accacttggc aagagtggta agctatataa   10260
aaaaatgaac attattacga gatgttatat gccattatat tgattcgaag atatatgttt   10320
ctttctccca cgggcaccta acggatacat gataaggcca aggcagatca cgggaaatta   10380
ttcgaataca tgttacgccc tattgccgga aaaaaaatgc agggcaggtg ttggccgtag   10440
cgatttaagc acttaagctg gaggttgcca cacttggatg caagcgtctg acccttctaa   10500
aaaatcggcg gctttgtccg tatccgtatc ccctatccaa catctagctg gccacacgac   10560
ggggctgggc agatcgtgga tgccgggtcg acgtcgatcg tcagccatca tagaccaatc   10620
gaccatctgt tatggatgct tgctagctag actagtcaga cataaaattt ggatactttc   10680
tcccaactgg gagacgggga ctgatgtgca gctgcacgtg agctaaattt ttccctataa   10740
atatgcatga aatactggcat tatcttgcca cagccactgc cacagccaga taacaagtgc   10800
agctggtagc acgcaacgca tagctctgga cttgtagcta ggtagccaac cgccacacga   10860
caccatgctc gacaccaaca aggtgtacga gatcagcaac cacgccaacg gcctctacgc   10920
cgccacctac ctctccctcg acgactccgg cgtgtccctc atgaacaaga acgacgacga   10980
catcgacgac tacaacctca agtggttcct cttcccgatc gacgacgacc agtacatcat   11040
cacctcctac gccgccaaca actgcaaggt gtggaacgtg aacaacgaca agatcaacgt   11100
gtccacctac tcctccacca actccatcca gaagtggcag atcaaggcca acggctcctc   11160
ctacgtgatc cagtccgaca acggcaaggt gctcaccgcc ggcaccggcc aggccctcgg   11220
cctcatccgc ctcaccgacg agtcctccaa caacccgaac cagcagtgga acctgacgtc   11280
cgtgcagacc atccagctcc cgcagaagcc gatcatcgac accaagctca aggactaccc   11340
gaagtactcc ccgaccggca acatcgacaa cggcacctcc ccgcagctca tgggctggac   11400
cctcgtgccg tgcatcatgg tgaacgaccc gaacatcgac aagaacaccc agatcaagac   11460
cacccccgtac tacatcctca agaagtacca gtactggcag agggccgtgg gctccaacgt   11520
cgcgctccgc ccgcacgaga agaagtccta cacctacgag tggggcaccg agatcgacca   11580
gaagaccacc atcatcaaca ccctcggctt ccagatcaac atcgacagcg gcatgaagtt   11640
cgacatcccg gaggtgggcg gcggtaccga cgagatcaag acccagctca acgaggagct   11700
caagatcgag tactcccacg agacgaagat catggagaag taccaggagc agtccgagat   11760
cgacaacccg accgaccagt ccatgaactc catcggcttc ctcaccatca cctccctgga   11820
gctctaccgc tacaacggct ccgagatccg catcatgcag atccagacct ccgacaacga   11880
cacctacaac gtgacctcct acccgaacca ccagcaggcc ctgctgtgag tagttagctt   11940
aatcacctag aacctagact tgtccatctt ctggattggc caacttaatt aatgtatgaa   12000
ataaaaggat gcacacatag tgacatgcta atcactataa tgtgggcatc aaagttgtgt   12060
gttatgtgta attactagtt atctgaataa aagagaaaga gatcatccat atttcttatc   12120
ctaaatgaat gtcacgtgtc tttataattc tttgatgaac cagatgcatt tcattaacca   12180
aatccatata catataaaata ttaatcatat ataattaata tcaattgggt tagcaaaaca   12240
aatctagtct aggtgtgttt tgcccttggc cacggtggcc agatccacta gaggcgcgcc   12300
tctagtgcgg ccgcttaatt aacttactag tgctagcctc gaggtcgact ctgatcatgg   12360
atgctacgtc acggcagtac aggactatca tcttgaaagt cgattgagca tcgaaaccca   12420
gctttcttgt acaaagtggt tgcggccgct taattaaatt aaatccaag cttgggctgc   12480
agatccccgg ggatctccgc ggagtatcgg aagttgaaga caaagaaggt cttaaatcct   12540
ggctagcaac actgaactat gccagaaacc acatcaaagc atatcggcaa gcttcttggc   12600
ccattatatc caaagacctc agagaaaggt gagcgaaggc tcaattcaga agattggaag   12660
ctgatcaata ggatcaagac aatggtgaga acgcttccaa atctcactat tccaccagaa   12720
gatgcataca ttatcattga aacagatgca tgtgcaactg gatggggagc agtatgcaag   12780
tggaagaaaa acaaggcaga cccaagaaat acagagcaaa tctgtaggta tgccagtgga   12840
aaaatttgata agccaaaagg aacctgtgat gcagaaatct atggggttat gaatggctta   12900
gaaaagatga gattgttcta cttggacaaa agagagatca cagtcagaac tgacagtagt   12960
gcaatcgaaa ggttctacaa caagagtgct gaacacaagc cttctgagat cagatggatc   13020
aggttcatgg actacatcac tggtgcagga ccagagatag tcattgaaca cataaaaggg   13080
aagagcaatg gtttagctga catcttgtcc aggctcaaag ccaaattagc tcagaatgaa   13140
ccaacggaag agatgatcct gcttacacaa gccataaggg aagtaattcc ttatccagat   13200
catcccataca ctgagcaact cagagaatgg ggaaacaaaa ttctggatcc attccccaca   13260
ttcaagaagg acatgttcga aagaacagag caagctttta tgctaacaga ggaaccagtt   13320
ctactctgtg catgcaggaa gcctgcaatt cagttagtgt ccagaacatc tgccaaccca   13380
ggaaggaaat tcttcaagtg cgcaatgaac aaatgccatt gctggtactg ggcagatctc   13440
attgaagaac acattcaaga cagaattgat gaatttctca agaatcttga agttctgaag   13500
accggtggcg tgcaaacaat ggaggaggaa cttatgaagg aagtcaccaa gctgaagata   13560
gaagagcagg agttcgagga ataccaggcc acaccaaggg ctatgtcgcc agtagccgca   13620
gaagatgtgc tagatctcca agacgtaagc aatgacgatt gaggaggcat tgacgtcagg   13680
gatgaccgca gcggagagta ctgggcccat tcagtggatg ctccactgag ttgtattatt   13740
gtgtgctttt cggacaagtg tgctgtccac tttcttttgg cacctgtgcc actttattcc   13800
ttgtctgcca cgatgccttt gcttagcttg taagcaagga tcgcagtgcg tgtgtgacac   13860
cacccccctt ccgacgctct gcctatataa ggcaccgtct gtaagctctt acgatcatcg   13920
gtagttcacc aaggcccggg gtcggatcta gctgaaggct cgacaaggca gtccacggag   13980
gagctgatat ttggtggaca agctgtggat aggagcaacc ctatccctaa tataccagca   14040
ccaccaagtc agggcaatcc ccagatcacc ccagcagatt cgaagaaggt acagtacaca   14100
cacatgtata tatgtatgat gtatcccttc gatcgaaggc atgccttggt ataatcactg   14160
agtagtcatt ttattacttt gttttgacaa gtcagtagtt catccatttg tcccattttt   14220
tcagcttgga agtttggttg cactggcctt ggtctaataa ctgagtagtc attttattac   14280
gttgtttcga caagtcagta gctcatccat ctgtcccatt ttttcagcta ggaagtttgg   14340
ttgcactggc cttggactaa taactgatta gtcattttat tacattgttt cgacaagtca   14400
gtagctcatc catctgtccc attttttcagc taggaagttc ggatctgggg ccatttgttc   14460
caggcacggg ataagcattc agggatccaa ccatggctca tgctgccctc agccctctct   14520
cccaacgctt tgagagaata gctgtccagc cactcactgg tgtccttggt gctgagatca   14580
ctggagtgga cttgagggaa ccacttgatg acagcacctg gaatgagata ttggatgcct   14640
tccacactta ccaagtcatc tactttcctg gccaagcaat caccaatgag cagcacattg   14700
cattctcaag aaggtttgga ccagttgatc cagtgcctct tctcaagagc attgaaggct   14760
atccagaggt tcagatgatc cgcagagaag ccaatgagtc tggaagggtg attggtgatg   14820
actggcacac agactccact ttccttgatg cacctccagc tgctgttgtg atgagggcca   14880
```

-continued

```
tagatgttcc tgagcatggc ggagacactg ggttcctttc aatgtacaca gcttgggaga    14940
ccttgtctcc aaccatgcaa gccaccatcg aagggctcaa cgttgtgcac tctgccacac    15000
gtgtgttcgg ttccctctac caagcacaga accgtcgctt cagcaacacc tcagtcaagg    15060
tgatggatgt tgatgctggt gacagagaga cagtccatcc cttggttgtg actcatcctg    15120
gctctggaag gaaaggcctt tatgtgaatc aagtctactg tcagagaatt gagggcatga    15180
cagatgcaga atcaaagcca ttgcttcagt tcctctatga gcatgccacc agatttgact    15240
tcacttgccg tgtgaggtgg aagaaagacc aagtccttgt ctgggacaac ttgtgcacca    15300
tgcaccgtgc tgttcctgac tatgctggca agttcagata cttgactcgc accacagttg    15360
gtggagttag gcctgcccgc tgagtagtta gcttaatcac ctagagctcg gtcgcagcgt    15420
gtgcgtgtcc gtcgtacgtt ctggccggcc gggccttggg cgcgcgatca gaagcgttgc    15480
gttggcgtgt gtgtgcttct ggtttgcttt aattttacca agtttgtttc aaggtggatc    15540
gcgtggtcaa ggcccgtgtg ctttaaagac ccaccggcac tggcagtgag tgttgctgct    15600
tgtgtaggct ttggtacgta tgggctttat ttgcttctgg atgttgtgta ctacttgggt    15660
ttgttgaatt attatgagca gttgcgtatt gtaattcagc tgggctacct ggacattgtt    15720
atgtattaat aaatgctttg ctttcttcta aagatcttta agtgcttcta gagcatgcac    15780
atagacacac acatcatctc attgatgctt ggtaataatt gtcattagat tgtttttatg    15840
catagatgca ctcgaaatca gccaatttta gacaagtatc aaacgggatgt gacttcagta    15900
cattaaaaac gtccgcaatg tgttattaag ttgtctaagc gtcaatttga               15950
```

```
SEQ ID NO: 2              moltype = DNA   length = 8029
FEATURE                   Location/Qualifiers
misc_feature              1..8029
                          note = Gene expression cassetted from pDAB113068
source                    1..8029
                          mol_type = other DNA
                          organism = synthetic construct
SEQUENCE: 2
aattacaacg gtatatatcc tgccagtcag catcatcaca ccaaaagtta ggcccgaata    60
gtttgaaatt agaaagctcg caattgaggt ctacaggcca aattcgctct tagccgtaca    120
atattactca ccagatccta accggtgtga tcatggccg cgattaaaaa tctcaattat    180
atttggtcta atttagtttg gtattgagta aaacaaattc ggcgccatgc ccgggcaagc    240
ggccgcacaa gtttgtacaa aaaagcaggc tcaatcctgt ccctagtgga taaactgcaa    300
aaggcgtaac taatcaatca cctcgtccta atcctcgaat ctctcgtggt gcccgtctaa    360
tctcgcgatt ttgatgctcg tggtggaaag cgtaggagga tcccgtgcga gttagtctca    420
atctctcagg gtttcgtgcg attttagggt gatccacctc ttaatcgagt tacggtttcg    480
tgcgatttta gggtaatcct cttaatctct cattgattta gggtttcgtg agaatcgagg    540
tagggatctg tgttatttat atcgatctaa tagatggatt ggttttgaga ttgttctgtc    600
agatggggat tgtttcgata tattaccota atgatgtgtc agatggggat tgtttcgata    660
tattaccota atgatgtgtc agatggggat tgtttcgata tattaccota atgatggata    720
ataagagtag ttcacagtta tgttttgatc ctgccacata gtttgagttt tgtgatcaga    780
tttagtttca cttatttgtg cttagttcgg atgggattgt tctgatattg ttccaataga    840
tgaatagctc gttaggttaa aatctttagg ttgagttagg cgacacatag tttatttcct    900
ctggatttgg attggaattg tgttcttagt tttttttcccc tggatttgga ttggaattgt    960
gtggagctgg gttagagaat tacatctgta tcgtgtacac ctacttgaac tgtagagctt    1020
gggttctaag gtcaatttaa tctgtattgt atctggctct ttgcctagtt gaactgtagt    1080
gctgatgttg tactgtgttt ttttacccgt tttatttgct ttactcgtgc aaatcaaatc    1140
tgtcagatgc tagaactagg tggctttatt ctgtgttctt acatagatct gttgtcctgt    1200
agttacttat gtcagttttg ttattatctg aagatatttt tggttgttgc ttgttgatgt    1260
ggtgtgagct gtgagcagcg ctcttatgat taatgatgct gtccaattgt agtgtaatat    1320
gatgtgattg atatgttcat ctattttgag ctgacagtac cgatatcgta ggatctggtg    1380
ccaacttatt ctccagctgc tttttttttac ctatgttaat tccaatcctt tcttgcctct    1440
tccagatcca gataccacac gacaccatgt tggctcgcca aggaggatca ctgagagcct    1500
ctcagtgtaa cgctggcctc gcgagacgcg tggaggtggg agcgttggtt gttccgagac    1560
ccataagcgt caacgacgtg gttccccatg tctattcggc tcctctgagc gtcgcgagga    1620
ggtcgtgctc caagtcatcc atccgctcga ctcgcagact tcagacaacc gtctgctccg    1680
caagagggat gccagccttg tcgctgcctg gctcaaagtc gatcacggct agagcactct    1740
ttctcgcagc agcagccgac ggagtcacca cgcttgtgag accgctgcgg tcagacgaca    1800
ccgagggttt tgcggaaggc ctcgtcagac tgggctatcg ggttgggagg actcccgaca    1860
cgtggcaagt ggacggaagg ccacaaggtc cagcagttgc cgaggctgat gtgtattgta    1920
gagacggtgc aacaacggct aggttcctcc ccacactcgc agctgctgga cacgggacct    1980
acagatttga tgcctctccc cagatgagga gaaggccact gctgcctctt tctagggctt    2040
tgagggacct tggcgttgat cttcgccacg aggaagcgga agggcaccac cccttgaccg    2100
tgagagctgc tggagtcgag ggaggtgagg ttacactcga tgctggacag tcctctcagt    2160
acttgacggc actgctgctg ctcggtccgc tcacacgcca ggcgctgcgg attcgcctca    2220
ctgatctggt tagcgctccg tacgtggaga ttacacttgc gatgatgaga gcttttgggg    2280
tcgaggttgc acgcgaaggc gacgtttcg tggtgcctcc tggtggctac agagcgacta    2340
cgtacgcgat tgagccagat gccagcaccg caagctactt ctttgcagct gctgcgttga    2400
cacctggagc cgaggtcaca gtgcctggac tcgggaccgg agcgcttcaa ggggatctcg    2460
gcttcgtgga cgtgctgcgg aggatgggtg ccgaggtcag gacgctacga    2520
ctgttagagg cacgggtgag cttagaggcc ttacagcaaa catgagggac atatccgaca    2580
cgatgccgac gcttgctgcc atcgctccgt tcgcttcagc acccgtcaga attgaagatg    2640
tggcgaacac tcgcgtcaaa gagtgcgaca gacttgaagc gtgtgccgag aacttgagga    2700
ggttgggagt gagagtcgca actggtccag actggatcga gatccaccct ggtccagcta    2760
ctggagcgca agtcacaagc tatgtgcgacc ataggattgt tatgtcattc gcagtgaccg    2820
gactcagagt tcctgggatc tctttcgacg accctggttg cgtgcggaaa acgttccctg    2880
gcttccacga ggcatttgcg gagctgcgga gaggaattgg ttcctgagta gttagcttaa    2940
tcacctagag ctcggtcgca gcgtgtgcgt gtccgtcgta cgttctggcc ggccgggcct    3000
tgggcgcgcg atcagaagcg ttgcgttggc gtgtgtgtgc ttctggtttg ctttaattt    3060
accaagtttg tttcaaggtg gatcgcgtgg tcaaggcccg tgtgctttaa agacccaccg    3120
```

-continued

```
gcactggcag tgagtgttgc tgcttgtgta ggctttggta cgtatgggct ttatttgctt  3180
ctggatgttg tgtactactt gggtttgttg aattattatg agcagttgcg tattgtaatt  3240
cagctgggct acctggacat tgttatgtat taataaatgc tttgctttct tctaaagatc  3300
tttaagtgct gccttttgca gtttatctct atgcccggga caagtgcaat cctgtcccta  3360
gtgagatggg cgggagtctt ccagatctgg ttaatgaggg aaagtaatct acagaagtac  3420
agtcccctct gaaaggaaca tggcttatac tccatgcctt caagtagatt tgaagtcatt  3480
gcttcactta ggaagttcta ttgtttgaga tggtggttat gacaggctcc gtttaaactt  3540
gctggtgtta tgtgcccttg aagtagccag gaggtttgtt gttcccatac acccatgagg  3600
gcttggtcag ttttctctgg tatgttactg gatggagagg gtctccaagt gtgcaatgtg  3660
aacttaacaa catcccaggg cactcacccc tcactgactt ttttggctac taataaacag  3720
actagctatc attcaccttt gtagccagaa tcccagggga tctgcaccca gtactcattc  3780
cagcttgcag aataatatcc accaggtcat gtaataagag gagtcaagga cttagtcttg  3840
tttcctcact catcaattat gaggtattgc catgatgcct agccacctca cacaacctag  3900
acaaggccac tgtgtccaag actcattcac ccagtcacta gcacccagtc ttgcacccag  3960
gggggttctg gaggccctcc aaatactaag taacatttt ccaggcacac aatgtgtgag  4020
taggacacag tgcagttgat caaacccagg tttcttgtgt agtgccttcc ctattgagga  4080
ccagggagca tggccacctc tcaaagtcag ctctcatcaa tctctcaaca aactgtttac  4140
atattatctc tgattcccag gaggactcag ccccacaact tcccatttca ggtatccctt  4200
ggcatcctag ccctaatgcc catttgttaa tatgggatgg ctcacctctg aggactctag  4260
ttacagggtg gagtctccct tgggatttca gttggtaggt taaaaatggg agtggcatgg  4320
agaggaaata acagaggccc tccagcaata gcttctctgt gatgataacc cctatactct  4380
atattttaca atcctgtccc tagtggataa actgcaaaag cacccagct ttcttgtaca  4440
aagtggttgc ggccgcttaa ttaaatttaa atgtttgggg atcctctaga gtcgacctgc  4500
agtgcagcgt gacccggtcg tgcccctctc tagagataat gagcattgca tgtctaagtt  4560
ataaaaaatt accacatatt tttttgtca cacttgtttg aagtgcagtt tatctatctt  4620
tatacatata tttaaacttt actctacgaa taatataatc tatagtacta caataaatc  4680
agtgttttag agaatcatat aaatgaacag ttagacatgg tctaaaggac aattgagtat  4740
tttgacaaca ggactctaca gttttatctt tttagtgtgc atgtgttctc ctttttttt  4800
gcaaatagct tcacctatat aatacttcat ccatttttatt agtacatcca tttagggttt  4860
agggttaatg gttttttatag actaatttt ttagtacatc tattttattc tattttagcc  4920
tctaaattaa gaaaactaaa actctatttt agttttttta tttaatagtt tagatataaa  4980
atagaataaa ataaagtgac taaaaattaa acaaataccc tttaagaaat taaaaaaact  5040
aaggaaacat ttttcttgtt tcgagtagat aatgccagcc tgttaaacgc cgtcgacgag  5100
tctaacggac accaaccagc gaaccagcag cgtcgcgtcg ggccaagcga agcagacggc  5160
acggcatctc tgtcgctgcc tctggacccc tctcgagagt tccgctccac cgttggactt  5220
gctccgctgt cggcatccag aaattgcgtg gcggagcggc agacgtgagc cggcacggca  5280
ggcggcctcc tcctcctctc acggcaccgg cagctacggg ggattcctt cccaccgctc  5340
cttcgctttc ccttcctcgc ccgccgtaat aaatagacac ccctccaca ccctctttcc  5400
ccaacctcgt gttgttcgga gcgcacacac acacaaccag atctccccca aatccacccg  5460
tcggcacctc cgcttcaagg tacgccgctc gtcctccccc cccccccccc tctctacctt  5520
ctctagatcg gcgttccggt ccatgcatgg ttagggcccg gtagttctac ttctgttcat  5580
gtttgtgtta gatccgtgtt tgtgttagat ccgtgctgct agcgttcgta cacggatgcg  5640
acctgtacgt cagacacgtt ctgattgcta acttgccagt gttctctttt ggggaatcct  5700
gggatggctc tagccgttcc gcagacggga tcgatttcat gatttttttt gtttcgttgc  5760
ataggggtttg gtttgcccctt ttcctttatt tcaatatatg ccgtgcactt gtttgtcggg  5820
tcatctttc atgctttttt ttgtcttggt tgtgatgatg tggtctggtt gggcggtcgt  5880
tctagatcgg agtagaattc tgtttcaaac tacctggtgg atttattaat tttggatctg  5940
tatgtgtgtg ccatacatat tcatagttac gaattgaaga tgatggatgg aaatatcgat  6000
ctaggatagg tatacatgtt gatgcgggtt ttactgatgc atatacagag atgcttttg  6060
ttcgcttggt tgtgatgatg tggtgtggtt gggcggtcgt tcattcgttc tagatcggag  6120
tagaatactg tttcaaacta cctggtgtat ttattaattt tggaactgta tgtgtgtgtc  6180
atacatcttc atagttacga gtttaagatg gatggaaata tcgatctagg ataggtatac  6240
atgttgatgt gggtttttact gatgcatata catgatggca tatgcagcat ctattcatat  6300
gctctaacct tgagtaccta tctattataa taaacaagta tgttttataa ttatttcgat  6360
cttgatatac ttggatgatg gcatatgcag cagctatatg tggatttttt tagccctgcc  6420
ttcatacgct atttatttgc ttggtactgt ttcttttgtc gatgctcacc ctgttgtttg  6480
gtgttacttc tgcagggtac agtagttagt tgacacgaca ccatgctccc ggagaggaga  6540
ccagttgaga ttaggccagc tacagcagct gatatggccg cggtttgtga tatcgttaac  6600
cattcattg agacgtctac agtgaacttt aggacagagc cacaaacacc acaagagtgg  6660
attgatgatc tagagaggtt gcaagataga taccccttggt tggttgctga ggttgagggt  6720
gttgtggctg gtattgctta cgctgggccc tggaaggcta ggaacgctta cgattggaca  6780
gttgagagta ctgtttacgt gtcacatagg catcaaaggt tgggcctagg atccacattg  6840
tacacacatt tgcttaagtc tatggaggcg caaggtttta agtctgtggt tgctgttata  6900
ggccttccaa acgatccatc tgttaggttg catgaggctt tgatacac agcccgtgtt  6960
acattgcgcg cagctggata caagcatggt ggatggcatg atgttggttt ttggcaaagg  7020
gattttgagt tgccagctcc tccaaggcca gttaggccag ttacccagat ctgactgagc  7080
ttgagcttat gagcttatga gcttagagct cggtcgcagc gtgtgcgtgt ccgtcgtacg  7140
ttctggccgg ccgggccttg ggcgcgcgat cagaagcgtt gcgttggcgt gtgtgtgctt  7200
ctggtttgct ttaattttac caagtttgtt tcaaggtgga cgtgtggga aaggcccgtg  7260
tgctttaaag acccaccggc actggcagtg agtgttgctg cttgtgtagg ctttggtacg  7320
tatgggcttt atttgcttct ggatgttgtg tactacttgg gtttgttgaa ttattatgag  7380
cagttgcgta ttgtaattca gctgggctac ctggacattt tatgtatta ataaatgctt  7440
tgctttcttc taaagatctt taagtgcttc tagagcatgc acatagacac acacatcatc  7500
tcattgatgc ttggtaataa ttgtcattag attgtttta tgcatagatg cactcgaaat  7560
cagccaattt tagacaagta tcaaacggat gtgacttcag tacattaaaa acgtccgcaa  7620
tgtgttatta agttgtctaa gcgtcaattt gatttacaat tgaatatatc ctgcccagc  7680
cagccaacag ctcgatttac aattgaatat atcctgccgg ccggcccacg cgtgtcgagg  7740
aattctgatc tggccccccat ttggacgtga atgtagacac gtcgaaataa agatttccga  7800
attagaataa tttgtttatt gctttcgcct ataaatacga cggatcgtaa tttgtcgttt  7860
```

-continued

```
tatcaaaatg tactttcatt ttataataac gctgcggaca tctacatttt tgaattgaaa    7920
aaaaattggt aattactctt tcttttttctc catattgacc atcatactca ttgctgatcc    7980
atgtagattt cccggacatg aagccattta caattgaata tatcctgcc                 8029

SEQ ID NO: 3              moltype = DNA  length = 34
FEATURE                   Location/Qualifiers
misc_feature              1..34
                          note = ZFN binding site
source                    1..34
                          mol_type = other DNA
                          organism = synthetic construct
SEQUENCE: 3
caatcctgtc cctagtggat aaactgcaaa aggc                                 34
```